US007244578B2

(12) United States Patent
Hammond et al.

(10) Patent No.: US 7,244,578 B2
(45) Date of Patent: Jul. 17, 2007

(54) METHODS FOR MODELING INFECTIOUS DISEASE AND CHEMOSENSITIVITY IN CULTURED CELLS AND TISSUES

(75) Inventors: Timothy Grant Hammond, New Orleans, LA (US); Cheryl Anne Nickerson, River Ridge, LA (US)

(73) Assignees: Department of Veterans Affairs, Washington, DC (US); Administrators of the Tulane Education Fund, New Orleans, LA (US)

( * ) Notice: Subject to any disclaimer, the term of this patent is extended or adjusted under 35 U.S.C. 154(b) by 0 days.

(21) Appl. No.: 10/474,075

(22) PCT Filed: Apr. 5, 2002

(86) PCT No.: PCT/US02/11088

§ 371 (c)(1),
(2), (4) Date: Apr. 26, 2004

(87) PCT Pub. No.: WO02/081734

PCT Pub. Date: Oct. 17, 2002

(65) Prior Publication Data

US 2004/0175707 A1    Sep. 9, 2004

Related U.S. Application Data

(60) Provisional application No. 60/282,007, filed on Apr. 6, 2001.

(51) Int. Cl.
*C12Q 1/70* (2006.01)
(52) U.S. Cl. .................. 435/7.21; 435/5; 435/70.1; 435/70.3
(58) Field of Classification Search ............ 435/5, 435/7.21, 70.1, 70.3, 375, 394, 403
See application file for complete search history.

(56) References Cited

U.S. PATENT DOCUMENTS 6,117,674 A    9/2000  Goodwin et al. ........... 435/325
6,730,498 B1 *  5/2004  Goodwin et al. .......... 435/69.1

FOREIGN PATENT DOCUMENTS

WO    WO02/081734    10/2002

OTHER PUBLICATIONS

Institute of Food Science and Technology, IFST: Current Hot Topics, Nov. 11, 1997, pp. 1-6, http://www.ifst.org/hottop20.htm.*
Medline Plus, Drug Information: Gentamicin (Topical), last updated on Jun. 8, 1994, pp. 1-3, available from the following: http://www.nlm.nih.gov/medlineplus/print/druginfo/uspdi/202258.html).*
McSorely, Stephen J. et al., Characterization of CD4 T Cell Responses During Natural Infection with *Salmonella typhimurium*, The Journal of Immunology, 2000, 164:986-993.*
International Search Report for PCT/US02/11088 mailed Sep. 12, 2002, 2 pp.
Bakos A, Varkonyi A, Minarovits J and Batkai L. 2002. Effect of Simulated Microgravity on the Production of IL-12 by PBMC's. J Gravit Physiol. 9(1): 293-4.
Bhat GK, Yang H and Sridaran R. 2001. Simulated Conditions Of Microgravity Suppress Progesterone Production by Luteal Cells of the Pregnant Rat. J Gravit Physiol 8: 57-66.
Botchwey EA, Pollack SR, Levine EM and Laurencin CT. 2001. Bone Tissue Engineering in a Rotating Bioreactor Using a Microcarrier Matrix System. J Biomed Mater Res 55: 242-53.
Cameron DF, Hushen JJ, and Nazian SJ. 2001. Formation of Insulin-Secreting, Sertoli-Enriched Tissue Constructs by Microgravity Cocultures of Isolated Pig Islets and Rat Sertoli cells. In Vitro Cell Dev Biol Anim 37: 490-8.
Clejan S. O'Connor K and Rosenweig N. 2001. Tri-dimensional Prostate Cell Cultures in Simulated Microgravity and Induced Changes in Lipid Second Messengers and Signal Transduction. J Cell Mol Med 5: 60-73.
Cowger NL, O'Connor KC and Bivins JE. 1997. Influence of Simulated Microgravity on the Longevity of Insect-Cell Culture. Enzyme and Microbial Technology 20: 326-332.
Cowger NL, O'Connor KC, Hammond TG, Lacks DJ and Navar GL. 1999. Characterization of Bimodal Cell Death of Insect Cells in a Rotating-Wall Vessel and Shaker Flask. Biotechnol Bioeng 64: 14-26.

(Continued)

*Primary Examiner*—Stacy B. Chen
(74) *Attorney, Agent, or Firm*—Locke Liddell & Sapp LLP

(57)    ABSTRACT

The present invention provides methods for utilizing a form of optimized suspension culture to examine the infectivity of pathogenic organisms and agents in human cells and tissues. Also provided are methods using a rotating wall vessel to predict chemosensitivity of cells and tissues to toxins and chemotherapeutic agents. These culture conditions potentiate spatial colocalization and three-dimensional assembly of individual cells into large aggregates which more closely resemble the in vivo tissue equivalent. In this environment, dissociated cells can assemble and differentiate into macroscopic tissue aggregates several millimeters in size. These culture conditions allow for better cellular differentiation and formation of three-dimensional cellular aggregates, more efficient cell-to-cell interactions, the in in vivo-like exchange of growth factors and greater molecular scaffolding facilitating mechanical stability for cells. The suspension culture system offers a new approach for studying microbial infectivity from the perspective of the host-pathogen interaction and also for analyzing chemosensitivity to toxins and chemotherapeutic agents.

25 Claims, 10 Drawing Sheets

OTHER PUBLICATIONS

Dabos KJ, Nelson LJ, Bradnock TJ, Parkinson JA, Sadler IH, Hayes PC and Plevris JN. 2001. The Simulated Microgravity Environment Maintains Key Metabolic Functions and Promotes Aggregation of Primary Porcine Hepatocytes. Biochem Biophys Acta 1526: 119-30.

Doolin EJ, Geldziler B, Strande L, Kain M, Hewitt C. Dec. 1999. Effects of Microgravity on Growing Cultured Skin Constructs. Tissue Eng 5 (6): 573-82.

Duke PJ, Daane EL, Montufar-Solis D. 1993. Studies of Chondrogenesis in Rotating Systems. J Cell Biochem 51: 274-82.

Duke PJ, Daane E, Arizpe J and Montufar-Solis D. 1996. Chondrogenesis in Aggregates of Embryonic Limb Cells Grown in a Rotating Wall Vessel. Adv. Space Research 17: 289-93.

Falsafi S and Koch RJ. 2000. Growth of Tissue-Engineered Human Nasoseptal Cartilage in Simulated Microgravity. Arch Otolaryngol Head Neck Surg 126: 759-65.

Felix JA, Dirksen ER and Woodruff ML. 2000. Selected Contribution: PKC Activation Inhibits Ca(2+) Signaling in Tracheal Epithelial Cells Kept in Simulated Microgravity. J Appl Physiol 89 (2): 855-64.

Francis KM, O'Connor KC and Spaulding GF. 1997. Cultivation of Fall Armyworm Ovary Cells in Simulated Microgravity. In Vitro Cell Dev Bio Anim 33: 332-6.

Freed LE, Hollander AP, Martin I, Barry JR, Langer R and Vunjak-Novakovic G. 1998. Chondrogenesis in a Cell-Polymer Bioreactor system. Exp Cell Res 240: 58-65.

Freed L, Martin I and Vunjak-Novakovic G. 1999. Frontiers in Tissue Engineering -In Vitro Modulation of Chondrogenesis. Clinical Orthopedics and Related Research 367S: S46-S58.

Goodwin TJ, Schroeder WF, Wolf DA and Moyer MP. 1993. Rotating-Wall Vessel Co-culture Of Small Intestine As A Prelude To Tissue Modeling: Aspects of Simulated Microgravity. Proc Soc Exp Biol Med 202: 181-92.

Goodwin TJ, Coate-Li L, Linnehan RM, and Hammond TG. 2000. Selected Contribution: a Three-Dimensional Model for Assessment of In Vitro Toxicity in Balena Mysticetus Renal Tissue. J Appl Physiol 89:2508-17.

Hales NW, Yamauchi K, Martinez AA, Sundaresan A, Pellis NR and Kulkarni AD. 2002. A Countermeasure to Ameliorate Immune Dysfunction in In Vitro Simulated Microgravity Environment: Role of Cellular Nucleotide Nutrition. In Vitro Cell Dev Biol (Animal) 38(4): 213-217.

Hughes JH and Long JP. 2001. Simulated Microgravity Impairs Respiratory Burst Activity in Human Promyelocytic Cells. In Vitro Cell Dev Biol Anim 37: 209-15.

Ingram M, Techy GB, Saroufeem R, Yazan O, Narayan KS, Goodwin TJ and Spaulding GF. 1997. Three-Dimensional Growth Patterns of Various Human Tumor Cell Lines in Simulated Microgravity of a NASA Bioreactor. In Vitro Cell Dev Biol Anim 33: 459-66.

Jessup JM, Frantz M, Sonmez-Alpan E, Locker J, Skena K, Waller H, Battle P, Nachman A, Bhatti, Weber ME, Thomas DA, Curbeam RL, Baker TL, and Goodwin TJ. 2000. Microgravity Culture Reduces Apoptosis and Increases the Differentiation of a Human Colorectal Carcinoma Cell Line. In Vitro Cell Dev Biol 36: 367-73.

Licato LL, Prieto VG, and Grimm EA. 2001. A Novel Preclinical Model of Human Malignant Melanoma Utilizing Bioreactor Rotating-Wall Vessels. In Vitro Cell Dev Biol Anim 37: 121-126.

Long JP and Hughes JH. 2001. Epstein-Barr Virus Latently Infected Cells are Selectively Deleted in Simulated-Microgravity Cultures. In Vitro Cell Dev Biol Anim 37: 223-230.

Long JP, Pierson S and Hughes JH. 1998. Rhinovirus Replication in HeLa Cells Cultured Under Conditions of Simulated Microgravity. Aviat Space Environ Med 69: 851-6.

Long JP, Pierson S and Hughes JH. 1999. Suppression of Epstein-Barr Virus Reactivation in Lymphoblastoid Cells Cultured in Simulated Microgravity. In Vitro Cell Dev Biol Anim 35: 49-54.

Low HP, Savarese TM and Schwartz WJ. 2001. Neural Precursor Cells Form Rudimentary Tissue-Like Structures in a Rotating-Wall Vessel Bioreactor. In Vitro Cell Dev Biol Anim 37: 141-147.

Margolis L, Fitzgerald W, Glushakova S, Hatfill S, Amichay N, Baibakov B and Zimmerberg J. 1997. Lymphocyte Trafficking and HIV Infection of Human Lymphoid Tissue in a Rotating Wall Vessel Bioreactor. AIDS Res Hum Retroviruses 13: 1411-20.

Martin A, Zhou A, Gordon RE, Henderson SC, Schwartz AE, Friedman EW and Davies TF. 2000. Thyroid Organoid Formation in Simulated Microgravity: Influence of Keratinocyte Growth Factor. Thyroid 10: 481-7.

Moore R. 1990. Comparative Effectiveness of a Clinostat and a Slow-Turning Lateral Vessel at Mimicking the Ultrastructural Effects of Microgravity in Plant Cells. Ann Bot (Lond). 66: 541-9.

Moorman SJ, Cordova R and Davies SA. 2002. A Critical Period for Functional Vestibular Development in Zebrafish. Dev Dyn 223: 285-91.

Nickerson, C.A., Goodwin, T.J., Terlonge, J., Ott, C.M., Buchanan, K.L., Uicker, W.B., Emami, K., Cedor, C.L., Ramamurthy, R., Hammond, T., and D L. Pierson. 2001. Three-Dimensional Tissue Assemblies: Novel Models for the Study of *Salmonella enterica* Serovar Typhimurium Pathogenesis. Infect. Immun. 69: 7106-7120.

O'Connor KC. 1999. Three-Dimensional Cultures of Prostatic Cells: Tissue Models for the Development of Novel Anti-Cancer Therapies. Pharmaceutical Research 16: 486-93.

Papadaki M, Bursac N, Langer R, Merok J, Vunjak-Novakovic G, Freed LE. 2001. Tissue Engineering of Functional Cardiac-Muscle: Molecular, Structural, and Electrophysiological Studies. Am J Physiol Heart Physiol 280: H168-78.

Park JH, Lee JM and Park IS. 1999. Production of Recombinant Endostatin from Stably Transformed Drosophila melanogaster S2 Cells. Biotechnology Letters 21: 729-733.

Plett PA, Frankovitz SM, Abonour R, Orschell-Traycoff CM. 2001. Proliferation of Human Hematopoietic Bone Marrow Cells in Simulated Microgravity. In Vitro Cell Dev Biol Anim 37: 73-8.

Rhee H, Chang S, Garner T and Chung L. 1998. Three-Dimensional (3-D) Human Prostate Organoid Culture to Study Cell—Cell and Cell-Matrix Interaction: Irreversible Alterations of Prostate Epithelial Tumorigenicity, Growth Responsiveness to Androgen and Estrogen, and Growth Factors in Culture. J Urology 159 (Suppl) 5.

Rhee HW, Shau HE, Pathak S, Multani AS, Oennanen S, Visakorpi T, and Chung LWK. 2001. Permanent Phenotypic and Genotypic Changes of Prostate Cancer Cells Cultured In a Three-Dimensional Rotating-Wall Vessel. In Vitro Cell Dev Biol Anim 37: 127-140.

Rutsky L, Bilinzki Z, Kloc M, Phan T, Zhang H, Katz S and Stepkowski S. 2002. Microgravity Culture Conditions Reduces Immunogenicity And Improves Function Of Pancreatic Islets. Transplantation 74: 13-21.

Saarinen MA and Murhammer DW. 2000. Culture in the Rotating-Wall Vessel Affects Recombinant Protein Production Capability of Two Insect Cell Lines in Different Manners. In Vitro Cell Dev Biol Anim 36: 362-6.

Savary C, Grazziuti ML, Przeplorka D, Tomasovic SP, McIntyre BW, Woodside DG, Pellis NR, Pierson DL, Rex JH. 2001. Characteristics of Human Dendritic Cells Generated in a Microgravity Analog Culture System. In Vitro Cell Dev Biol Anim Apr. 2001 37(4): 216-22.

Slentz DH, Truskey GA, and Kraus WE. 2001. Effects of Chronic Exposure to Simulated Microgravity on Skeletal Muscle Cell Proliferation. In Vitro Cell Dev Biol Anim 37: 148-156.

Sytkowski AJ and Davis KL. 2001. Erythroid Cell Growth and Differentiation In Vitro in the Simulated Microgravity Environment of the NASA Rotating Wall Vessel Bioreactor. In Vitro Cell Dev Biol Anim 37: 79-83.

Tobin BW, Leeper-Woodfored SK, Hashemi BB, Smith SM, and Sams CF. 2001. Altered TNF-Alpha, Glucose, Insulin, and Amino Acids in Islets of Langerhans Cultured in a Microgravity Model System. Am J Physiol Endocrinol Metab 280: E92-102.

Van Luyn MA, Tio RA, Gallego y van Seijen XJ, Plantinga JA, de Leij LFMH, DeJongste ML, and van Wachem PB. 2002. Cardiac Tissue Engineering: Characteristics of in Unison Contracting Two- and Three-dimensional Neonatal Rat Ventricle Cell (Co)-Cultures. Biomaterials 23: 4793-4801.

Duray PH, Hatfill SJ and Pellis NR. 1997. Tissue Culture in Microgravity. Science & Medicine, May/Jun. 1997: 45-55.

Freed LE and Vunjak-Novakovic G. 2002. Spaceflight Bioreactor Studies of Cells and Tissues. Cell Biol. Biotech. Space: 177-95.

Hammond TG, and Hammond JM. 2001. Optimized Suspension Culture: The Rotating-Wall Vessel. Am J Physiol Renal Physiol 281: F12-F25.

Unsworth BR and Leikes PI. 1998. The Use of Rotating Wall Bioreactors for the Assembly of Differentiated Tissue-Like Organoids. Advances in Tissue Engineering: New developments in cartilage, skin and bone engineering, Chapt. 2.3, pp. 113-132.

Vunjak-Novakovic G, Obradovic B, Martin I and Freed LE. 2002. Bioreactor Studies of Native and Tissue Engineered Cartilage. Biorheology 39: 259-68.

* cited by examiner

METHODS FOR MODELING INFECTIOUS DISEASE AND CHEMOSENSITIVITY IN CULTURED CELLS AND TISSUES

CROSS REFERENCES TO RELATED APPLICATIONS

This application claims priority to U.S. Provisional Application Ser. No. 60/282,007, filed Apr. 6, 2001, which is fully incorporated by reference herein.

STATEMENT REGARDING FEDERALLY SPONSORED RESEARCH

The invention was made in part with United States Government support awarded by the Department of Veterans Affairs and National Aeronautics and Space Administration. The U.S. Government has certain rights in the invention.

BACKGROUND OF THE INVENTION

1. Technical Field of the Invention

The present invention relates generally to the fields of microbiology, infectious diseases and drug toxicity. More specifically, the present invention relates to methods of modeling infectious disease and chemosensitivity with three-dimensional suspension of mammalian cells using a bioreactor.

2. Description of the Prior Art

An essential feature of the pathogenicity of microorganisms is their ability to infect or colonize host epithelial cells and cells in other tissues. The terms "infect" and "colonize" are used interchangeably herein, and encompass adherence to cells, invasion, survival within, and damage or destruction of the cells. Initial sites of bacterial infection include the epithelia of the intestine, kidney, lung and bladder. There is a need to investigate how bacterial and other pathogens interact with the epithelium to initiate disease, which can be through the use of both in vitro and in vivo models of infection.

Some types of tissue culture models of infectivity are not the best models of the conditions faced in vivo by pathogens. Conclusions drawn about the interaction between pathogens and the host epithelium using cultured epithelial cells may be limited due to the dedifferentiation of these cells during conventional cell culture. Many of the physiological differences between cultured cells and their in vivo counterparts are believed to be the result of the dissociation of cells from their native three-dimensional geometry in vivo to their propagation on a two-dimensional substrate in vitro. Likewise, many of the characteristics of animal models fail to mimic the human disease, and animal models present a complex system in which many variables cannot be controlled. Accordingly, since certain in vitro nor in vivo assays do not replicate the complex environment encountered by pathogens during the natural course of human infection, the information gained from these studies may be limited.

An essential feature of the pathogenicity of *Salmonella* is its ability to invade host intestinal epithelial cells. While important advances have been made toward understanding how *Salmonella* interacts with the intestinal epithelium to initiate disease, through the use of both in vitro and in vivo models of infection, numerous questions have been derived from these studies which remain to be answered. In particular, it is well-documented that important differences exist between the pathogenesis of serovar *Typhimurium* in human infections and in widely-used cell culture and animal models. Specifically, tissue culture models of infectivity are not exact models of the conditions faced in vivo by *Salmonella*. Conclusions drawn about the interaction between *Salmonella* and the host intestinal epithelium using cultured enterocytes are limited due to the dedifferentiation of these cells during conventional cell culture. Many of the physiological differences between cultured cells and their in vivo counterparts are believed to be the result of the dissociation of cells from their native three-dimensional geometry in vivo to their propagation on a two-dimensional substrate in: vitro. Likewise, many characteristics of animal models fail to mimic the human disease, and animal models present a complex system in which many variables cannot be controlled. Accordingly, since neither in vitro nor ill vivo assays faithfully replicate the complex environment encountered by *Salmonella* during the natural course of human infection, the information gained from these studies is limited. A high fidelity enteric cell culture model can provide new insights into studies of *Salmonella* infectivity by bridging the gap between the inherent limitations of cultured mammalian cells and intact animals.

The response of cells to various drugs is an area of great interest to the medical field. Currently, many model systems exist for testing the chemosensitivity of cells to various chemical compounds in order to identify new pharmaceutical agents for the treatment of cancer and other diseases. Conventional cell culturing techniques do not always accurately simulate conditions ill vivo favorable for the growth of some tissues. Hence, some biological properties affecting tissue response to drugs are not apparent with standard cell culturing methods.

U.S. Pat. No. 6,117,674, which is fully incorporated by reference herein, discloses an invention relating to the propagation of a pathogen selected from the group consisting of viruses, bacteria, protozoans, parasites and fungi, by inoculating a three dimensional tissue mass culture at microgravity conditions in fluid culture media in a microgravity vessel with the pathogen. Specifically, the microgravity conditions are simulated in unit gravity by a horizontal rotating wall vessel (RWV). Growth conditions in the RWV allow for better cellular differentiation and formation of three-dimensional cellular aggregates, more efficient cell-to-cell interactions, the ill vivo-like exchange of growth factors and greater molecular scaffolding facilitating mechanical stability for cells. The RWV bioreactors offer a revolutionary approach not previously applied for studying microbial infectivity from the perspective of the host-pathogen interaction and also for analyzing chemosensitivity to toxins and chemotherapeutic agents, like antibiotics.

SUMMARY OF THE INVENTION

The present invention pertains to the use of a low shear stress suspension cell culture system to study the infectivity of pathogenic organisms and agents in human cells and tissues. The cell culture conditions potentiate spatial co-localization and three-dimensional assembly of individual cells into large aggregates, which more closely resemble the in vivo tissue equivalent. In this environment, dissociated cells can assemble and differentiate into macroscopic tissue aggregates several millimeters in size, which are largely devoid of necrotic cores. The present invention also provides methods for predicting the chemosensitivity of cells and tissues to toxins and chemotherapeutic agents. Use of the present invention to generate 3-D aggregates that closely resemble the "in vivo" tissue equivalent, from a variety of cell types has wide applications in the modeling of infectious diseases.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the invention presented herein.

DETAILED DESCRIPTION OF ILLUSTRATIVE EMBODIMENTS

Figure 1:
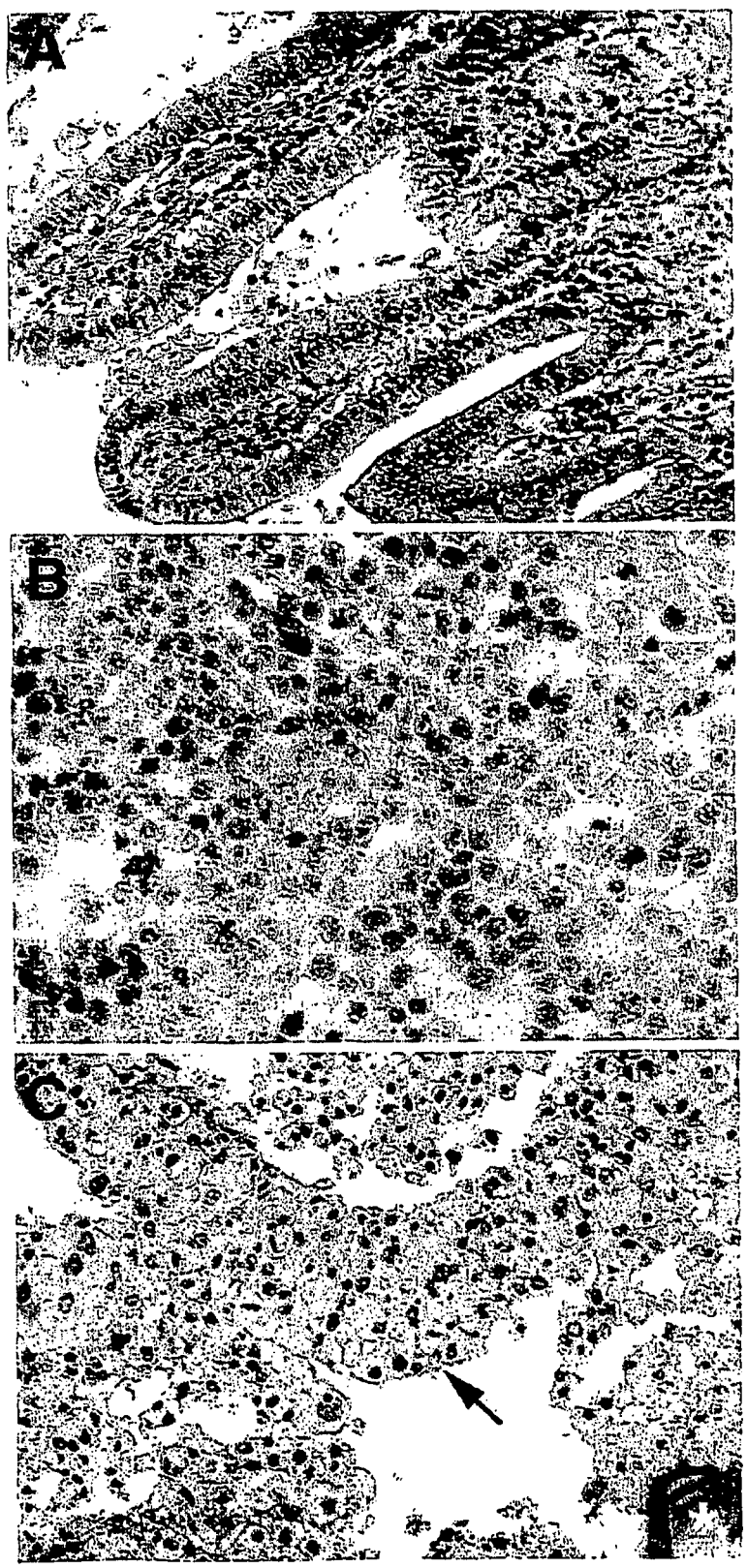
FIG. 1 shows a morphological comparison of paraffin-sectioned normal human small intestine (A), paraffin-embedded Int-407 (intestinal epithelial cell) monolayer cultures (B), and paraffin-sectioned Int-407 3-D aggregates (C) stained with hematoxylin-eosin. The three-dimensional organization is observed in a cross-section of an Int-407 3-D-construct (Panel C, arrow), morphologically reminiscent of the intestinal villi seen in normal small intestine (Panel A). In contrast, note the complete lack of organization observed when Int-407 cells are cultured as standard monolayers (Panel B). A sectioned micro-carrier bead can be seen in Panel C (*). All micrographs were obtained at 200× magnification.

The present invention relates to the growth of cells in a suspension culture that due to low shear and low operational turbulence minimizes mechanical cell damage and allows cells to associate into three-dimensional structures, thereby promoting cellular differentiation. In an aspect of the invention, the three-dimensional cell structures (or 3-D aggregates) are used to study microbial infectivity from the perspective of the host-pathogen interaction. In another aspect of the invention, the three dimensional cell structures are used to study the chemosensitivity of the 3-D tissue mass to chemotherapeutic agents and toxins.

The present invention further relates to the use of a bioreactor for the growth of cells in a suspension culture, wherein the shear levels are defined. Specifically, cell culture is carried out in the bioreactor under conditions of applied shear, Coriolis forces applied, with cells falling at a terminal velocity. This tissue culture approach permits the generation of 3-D differentiated tissue-like assemblies which model many aspects of in vivo human tissues, and thus offer a new approach for studying microbial infectivity from the perspective of host-pathogen interaction, and chemosensitivity of tissues to therapeutic agents and toxins.

Recent work with cultured epithelial cell lines has begun to elucidate the molecular mechanisms by which microbial pathogens like *Salmonella*, induce inflammation. While the exact model by which *Salmonella* triggers an infection remains incompletely-defined, results from both in vivo and in vitro studies suggest that, in response to *Salmonella* invasion, epithelial cells rapidly upregulate the expression and secretion of any array of cytokines known to be important for the initiation of an acute inflammatory response, including TNF-$\alpha$ and an array of proinflammatory mediators, like interleukin-8 (IL-8) and pathogen-elicited epithelial chemoattractant (PEEC), that chemoattract neutrophils and mononuclear phagocytes to the site of infection. Thus, in the early stages following *Salmonella* invasion, intestinal epithelial cells (for e.g., Int-407) produce mediators that have the potential to orchestrate the onset of the mucosa inflammatory response.

It is possible that the increased expression of the proinflammatory cytokines TNF-$\alpha$, and IL-6 by the Int-407 monolayers as compared to the 3-D aggregates in response to *Salmonella* infection is, in part, responsible for the dramatic increase in damage to the monolayers as compared to 3-D Int-407 tissue aggregates. Furthermore, the enhanced basal level of expression of TGF-$\beta$1 by the uninfected 3-D Int-407 cells as compared to monolayers is relevant to the in vivo condition, in which the intestinal mucosa constitutively produces high levels of this cytokine.

Int-407 monolayers respond to infection with *Salmonella* by increasing the transcriptional expression of genes encoding the proinflammatory and immunomodulatory cytokines IL-1$\alpha$, IL-1$\beta$, IL-6, and TNF-$\alpha$, the latter of which has been shown to induce apoptosis in several cell types. In contrast, 3-D Int-407 tissue aggregates infected with *Salmonella* increased expression of the antiinflammatory cytokine IL-1Ra. These results suggest that the relatively undifferentiated Int-407 monolayers react differently to infection with *Salmonella* than do the 3-D Int-407 tissue aggregates. Although infection of 3-D Int-407 tissue aggregates with *Salmonella* stimulated increased transcription of these same cytokines, the magnitude of induction of expression was markedly less as compared to Int-407 monolayers.

In vitro and in vivo studies have reported that, following infection with *Salmonella*, increased prostaglandin synthesis by PMNs and epithelial cells is important for the increased fluid secretion from intestinal epithelium. However, the role of prostaglandin in the development of *Salmonella*-induced diarrheal disease in humans has not been established. It has been suggested that, in addition to regulating gastrointestinal fluid secretion, epithelial-derived prostaglandin may limit the extent of mucosa injury following infection with invasive bacteria. While it is unclear as to how prostaglandin may exert mucosa-protective events, they have been shown to down-regulate the production of several proinflammatory cytokines, such as IL-1. The results from the studies are in agreement with a role for prostaglandin in mediating a protective response against *Salmonella*-induced damage to the epithelial mucosa. The constitutive levels of is $PGE_2$ synthesis in uninfected 3-D Int-407 cells is significantly higher than that observed for uninfected monolayer cultures.

In an aspect of the present invention, methods for utilizing a form of optimized suspension culture to examine the infectivity of pathogenic organisms and agents in cells and tissues are provided. Also provided are methods using a RWV to predict the chemosensitivity of cells and tissues to toxins and chemotherapeutic agents.

The invention is now described in detail with reference to specific embodiments. It will be understood that variations, which are functionally equivalent, are within the scope of this invention. Various modifications of the invention in addition to those shown and described herein will be apparent to those skilled in the art from the description herein and the accompanying drawings. Such modifications are intended to fall within the scope of the claimed invention.

The present invention encompasses methods for modeling infectious disease and chemosensitivity in cells and tissues. In an embodiment of the present invention, three-dimensional tissue masses are cultured in bioreactors or microgravity vessels, which provide low shear and essentially no relative motion of the culture environment with respect to the walls of the culture vessel.

In a further embodiment of the invention, tissues are grown in a rotating wall vessel (RWV) under conditions designed to allow the formation of three-dimensional cell aggregates rather than monolayers, and promote the cellular expression of special features and properties normally displayed in vivo. These three-dimensional tissue aggregates serve as a model for microbial infectivity by a bacterial pathogen and as a model to test chemosensitivity.

One aspect of the invention involves the co-culturing in a rotating wall vessel of tissue constructs and microorganisms to facilitate analysis of microorganism adhesion, invasion, virulence and growth. The microorganisms are placed in a RWV with culture medium along with tissue constructs, and cultured for a period of hours to days, after which parameters of the microorganism's effect on the tissues are assayed. These effects include microorganism growth, adherence, invasion, biofilm formation, cell toxicity and/or death. It has been proposed that up to 60–70% of all infectious diseases are mediated at some point in their time course by the formation of a microbial biofilm. The invention models the infectivity of tissues in vivo more accurately than monolayer cultures. Dramatic differences occur between cells cultured in a RWV compared to monolayer cultures in response to infection with a microorganism, including differences in adherence, invasion, apoptosis, cytokine expression, prostaglandin synthesis and tissue pathology. Hence, cultivation of host tissues and cells with natural pathogens in the RWV allows maintenance of both the differentiated features of the host tissues and the natural infectivity of the microorganisms.

In a separate aspect of the invention, the three dimensional aggregates can be infected with microorganisms outside the bioreactor environment. Specifically, the three dimensional aggregates are formed within the bioreactor, followed by seeding and propagation of the 3-D tissue constructs in standard tissue culture systems, after which the 3D tissues are infected with the pathogen.

An embodiment of the present invention provides a method of studying the infectivity of a pathogen in tissues comprising the steps of:
  isolating host cells;
  placing said isolated host cells into a rotating wall vessel comprising culture media;
  applying sedimental shear stress to the cells in the cell culture to form a three-dimensional tissue mass;
  introducing an infectious pathogen into said culture containing said three-dimensional tissue mass; and
  assaying the infectivity of said infectious pathogen.

A further embodiment of the present invention provides a method of studying the infectivity of a pathogen in tissues comprising the steps of:
  isolating intestinal epithelial cells;
  placing said intestinal epithelial cells into a rotating wall vessel comprising culture medium;
  applying sedimental shear stress to the cells in the cell culture to form a three-dimensional tissue mass;
  seeding the formed tissue mass in a tissue culture vessel; and,
  introducing an infectious pathogen to the formed tissue mass.

The above embodiments can optionally comprise the use of a culture matrix that would permit the adherence of the cells in the culture. Examples of such culture matrices consist of microbeads or microcarriers, including but not limited to, collagen-coated microbeads or polymer scaffolding. Furthermore, the infection of the 3D tissue mass with the microorganism and the chemosensitivity assays may be carried out either within the bioreactor or external to the bioreactor, under standard tissue culture conditions. Additionally, in a separate embodiment of the invention, an infecting microorganism is cultured either in the bioreactor or under standard laboratory conditions, prior to the introduction of host cells.

Another embodiment of the present invention provides a method of measuring the chemosensitivity of tissues to a toxic materials comprising:
  isolating host cells;
  placing said isolated host cells into a rotating wall vessel comprising culture medium;
  applying sedimental shear stress to the cells in the cell culture to form a three-dimensional tissue mass;
  introducing a toxic material into said culture containing said three-dimensional tissue mass; and
  assaying the chemosensitivity of said toxic material.

In an embodiment of the present invention, the toxic material is a chemotherapeutic material. In a further embodiment of the invention, the chemotherapeutic material is an antibiotic, more preferably gentamicin.

The present invention has a wide application for the modeling of infectious disease. Host tissues to be analyzed in the RWV infectivity experiments include, but are not limited to, epithelial tissues including those lining the gastrointestinal tract, as well as tissue from lung, kidney and liver. The infectivity of a number of pathogenic organisms can be analyzed including viruses, bacteria, protozoans, parasites and fungi. More specifically, the pathogens used include strains of *Salmonella typhimurium, Escherichia coli, Shigella, Yersinia, campylobacter, Vibrio* and other microbial pathogens like *Listeria monocytogenes*. Application of the invention includes the identification of candidate virulence genes, virulent serotypes for vaccine production and other therapeutic strategies, analysis of host responses to microbial infection, as well as in the in vitro demonstration of the efficacy of vaccines.

Another aspect of the invention involves the culturing of tissues and cells in a RWV as a method to measure the chemosensitivity of the culture to toxins and chemotherapeutic substances. Cells are cultured in the RWV for a period of time and then a test compound is introduced to the growing cells. There is a dramatic change in the sensitivity of cells and tissues cultured in a RWV to drugs and toxins. The invention demonstrates that cell aggregates or tissue explants grown in the RWV have properties characterized by a change in the dose of drugs or toxins, which cause cell changes such as apoptosis or necrosis. The present invention permits the realistic modeling of the in vivo sensitivity of a wide variety of cells including, but not limited to lung, kidney, liver, intestine and bladder. Application of the invention includes the development of protective agents for tissue toxicity, prediction of the response of patient specific cancers to chemotherapeutic agents and prediction of the toxic effects of therapeutics.

In humans, *S. enterica* serovar *Typhimurium* is among the most common *Salmonella* serotypes isolated from humans suffering from infectious gastroenteritis, and has long been recognized as a major public health problem. Gastroenteritis results from infection of the small intestine after ingestion with *Salmonella*. Following ingestion, *Salmonella* adheres to and invades into both the M cells of the Peyer's patches and the intestinal enterocytes. This ability to attach to and penetrate intestinal epithelium is an essential feature in the pathogenicity of *Salmonella* infection. The initial interactions between *Salmonella* and the host intestinal epithelium are believed to play a key role in mediating the intense inflammatory and secretory response which is a hallmark of serovar *Typhimurium* infections in humans. Both in vitro and in vivo studies have shown that the inflammatory response to *Salmonella* infection is characterized by an influx of polymorphonuclear leukocytes (PMNs) into the intestine and lumen resulting in a net increase in fluid secretion into the lumen. Studies with cultured intestinal epithelial cells have shown that, shortly after contact, *Salmonella* engages host cells in a complex biochemical cross-talk, which triggers host-cell signal transduction pathways ultimately resulting in host cytoskeleton rearrangement, cell membrane ruffling, bacterial uptake, and production of prostaglandins, and proinflammatory cytokines.

RWV bioreactors have been used to develop three-dimensional cultures of human intestinal epithelial cells which more accurately model the behavior of in vivo tissues as compared to monolayer cultures of the same cells, and thus would be predicted to more closely replicate the complex environment encountered by *Salmonella* during the natural course of human infection. The present invention that the 3-D intestinal cells react much differently to *Salmonella* infection as compared to conventional monolayers of the same cell line, including differences in bacterial adherence and invasion, apoptosis, cytokine expression, prostaglandin synthesis, and tissue pathology.

The following is a description of culturing and growing a representative bacterial strain, which can be used to practice the present invention. Representative infectivity studies were performed using wild-type *Salmonella enterica* serovar *Typhimurium*, χ3339, which is an animal passaged isolate of the virulent SLI344 wild-type. See Gulig and Curtiss, Infection and Immunity, 55: 2891–2901 (1987), which is fully incorporated by reference herein. Bacterial cells were first grown in Lennox broth (L-broth) as static overnight cultures at 37° C. Cultures were then inoculated at a dilution of 1:200 into 50 ml of L-broth and subsequently grown with aeration at 37° C. until reaching mid-log phase of growth. Unless otherwise stated, all infectivity studies were performed at a multiplicity of infection (MOI) of between one-to-10 bacteria per host cell.

The following is a description of the development of a three-dimensional tissue model. The human embryonic intestinal epithelial cell line Int-407 was obtained from the American Type Culture Collection (ATCC) (CCL-6) and was initially grown in Corning T-75 flasks ($2 \times 10^5$ cells/ml) at 37° C. in a 5% $CO_2$ environment in preparation for seeding into the RWV. The cells were cultured in a specialized growth medium comprised of a triple-sugar minimal essential medium-alpha/L-15 base supplemented with 6% fetal bovine serum (FBS), designated GTSF-2. After 24 hours, the spent media was removed, fresh GTSF-2 was added, and the cells were cultured until reaching approximately 70% confluency. Cells were then washed once with pre-warmed calcium-and magnesium-free phosphate-buffered saline (PBS), removed from the flask by treatment with 0.25% trypsin, and resuspended in fresh medium at a density of $2 \times 10^5$ cells/ml. The cells were assayed for viability by trypan blue dye exclusion. Cells were then introduced into the RWV (Synthecon, Inc.) containing 5 mg/ml Cytodex-3 microcarrier beads (Pharmacia), resulting in a final ratio of 10 cells/bead. Cytodex-3 microcarriers were Type 1, collagen-coated dextran beads (average diameter size 175 μm). Cells were cultured in the RWV bioreactors in GTSF-2 at 37° C. and 5% $CO_2$ with initial rotation at 20 rpm. Rotation speed was increased throughout growth to maintain cell aggregates in suspension. Cell growth was monitored daily by measurements of pH, dissolved $CO_2$ and $O_2$ and glucose utilization using a Corning Blood Gas Analyzer (Model 168) and a Beckman Glucose Analyzer 2, respectively. Fresh medium was replenished by 90% of the total vessel volume each 12–24 hr, depending upon the growth rate of the cultures. As metabolic requirements increased, fresh medium was supplemented with an additional 100 mg/dl of glucose. Immediately prior to use of the 3-D intestinal tissues, fresh medium was added to the cultures. For all studies, 3-D intestinal tissues were cultured in the RWVs for 28–32 days prior to their use.

Int-407 cells cultured as 3-D aggregates or as monolayers were subjected to immunohistochemical characterization. Samples for immunohistochemistry were taken from multiple experiments, fixed, and sectioned using method well known to one of ordinary skill in the art. Immunophenotyping was performed on 0.5 μm-thick sections of the 3-D Int-407 tissue aggregates, or monolayer culture controls, after extraction of the epoxy with melting solution for light microscopy studies. Slides of sectioned material were subsequently rehydrated and subjected to immunoperoxidase staining with panel of antibodies. To evaluate the mucin content, specimens were stained with periodic acid-Schiff (PAS).

Morphological comparisons between normal human small intestine, Int-407 monolayers, and 3-D Int-407 aggregates were determined from paraffin embedded sections of these samples stained with hematoxylin-eosin and analyzed via light microscopy.

For scanning electron microscopy (SEM) analysis, 3-D cell and monolayer samples were fixed in 4% glutaraldehyde. The samples were then immersed in 0.1% osmium tetroxide solution (Electron Microscopy Sciences) and dehydrated in a graded alcohol series to 100% ethanol. The 3-D cell aggregates were placed on a glass cover slip treated with 1% polyethyleneimine. Both 3-D cell cultures and monolayers were chemically treated with hexamethyldisilazane (Electron Microscopy Sciences) and allowed to dry. All cells were then mounted on specimen stubs and sputter coated with gold-palladium for observation in a JEOL 660T or Phillips XL-30 series scanning electron microscope.

For confocal imaging, samples were prepared as described using methods well know to one of ordinary skill in the art. Confocal imaging was performed using a Zeiss LSM 400 series laser scanning microscope. Fluorochrome excitation of Alexa 488 labeled secondary antibodies was by 488 nm filtered emission from a Kr-Argon laser source. Each image is the compilation of 16 scans of 2 seconds each, collected at identical exposure levels (the confocal pinhole size, laser output, filter settings and gain and contrast settings were held constant throughout). Each scan was corrected for background variations and noise by the LSM scanning software during the compilation process. This correction resulted in enhanced resolution, but did not affect exposure levels. Post-collection processing of the images was performed using Adobe PhotoShop. As before, no changes in image brightness or contrast were made.

For transmission electron microscopy (TEM) analysis, samples were prepared by methods well known to those of ordinary skill in the art. TEM imaging was performed using a JOEL 1010 series transmission electron microscope.

Adherence and invasion assays were conducted using methods well known to one of ordinary skill in the art, with the modification that 3-D Int-407 cells were seeded into 24-well tissue culture plates for infectivity assays. The number of cells associated with 3-D aggregates were determined. In an aspect of the invention, the infectivity assays are carried in the bioreactor or RWV, by co-culturing the tissue constructs and microorganisms.

The cytokine mRNA profiles expressed following *Salmonella* infection of 3-D Int-407 tissue aggregates and Int-407 monolayers were analyzed and quantified using a commercially available multiprobe RNAse protection assay (RiboQuant, PharMingen, San Diego, Calif.). Total RNA isolated from uninfected and infected 3-D intestinal aggregates and Int-407 monolayers was extracted using TriReagent in an acid guanidinium thiocyanate-phenol-chloroform method according to the manufacturer's instructions (Molecular Research Center, Inc., Cincinnati, Ohio). Total RNA was then used in RNAse protection assays with a mixture of [$^{32}$P]UTP-labeled antisense riboprobes generated from a panel of different human cytokine templates, specifically in this case, TNF-α, IL-1α, IL-1β, TNF-β, lymphotoxin-β IFNγ, IFNα, IL-6, IL-10, IL-12, IL-18 and TGF-β1. The template mixtures containing these cytokine templates also included templates for the housekeeping genes encoding glyceraldehyde-3-phosphate dehydrogenase (GAPDH) and L32 (a ribosomal protein) to ensure equal loading of total RNA onto 6% polyacrylamide/7M urea gels.

Quantification of each mRNA was accomplished with a Fuji FLA-3000 Phosphorimager and ImageGauge software. Each mRNA band was normalized to L32 or GADPH from the same RNA sample and the data presented as arbitrary units of each given cytokine.

In a prostaglandin immunoassay, levels of $PGE_2$ were determined in culture supernatants of infected and uninfected 3-D Int-407 cells seeded into 24-well tissue culture plates, and Int-407 monolayers by enzyme immunoassay according to the manufacturer's instructions (R&D Systems). Bacteria were prepared for infections as described above with an MOI of between 50:1 to 100:1. All Int-407 cells were infected for 1 h with χ3339, and cultured for an additional 7 h in the presence of gentamicin (10 μg/ml) to kill any remaining extracellular bacteria. Culture supernatants were sampled for $PGE_2$ expression prior to addition of *Salmonella*, and at 1, 2 and 8 h following infection.

Following incubation for 1.5 hours with or without *Salmonella*, Int-407 monolayers and 3-D aggregates were dissociated into individual cells by treatment with 0.1% EDTA for analysis of apoptosis. The cell number and viability were determined by trypan blue dye exclusion. The resulting single cell suspensions were washed with calcium-containing PBS and incubated for 15 minutes with FITC-conjugated Annexin V (R&D Systems) and/or propidium iodide to quantitate apoptosis and necrosis, respectively. Positive controls for apoptosis and necrosis were cultures of 3-D Int-407 tissue aggregates or monolayers cultured with actinomycin D (1 μg/ml) and sodium azide (1.0%), respectively. These control cells were incubated with actinomycin D or sodium azide for 2–3 h prior to washing and staining with FITC-Annexin V and propidium iodide and analysis on a FACS-Vantage flow cytometer.

Investigations into the interaction of *Salmonella* with the human intestinal epithelium have been limited by the lack of in vitro and in vivo models which faithfully replicate the in vivo condition. In particular, conventional tissue culture technology has failed to yield high-fidelity, multicellular three-dimensional models of intestinal epithelium which are suitable for investigations into *Salmonella*-induced gastroenteritis. A class of rotating bioreactors was used, which are optimized to minimize shear and turbulence, to culture 3-D human intestinal epithelial tissue retaining many differentiated features as a model to study the infectivity of the enteroinvasive pathogen *Salmonella*. The 3-D cultured human intestinal cells more accurately model in vivo tissues as compared to monolayer cultures of the same cells, and thus more closely replicate the complex environment encountered by *Salmonella* during the natural course of human infection. These observations are characterized by dramatic differences between the 3-D Int-407 cells and Int-407 monolayers in response to infection with *Salmonella*, including differences in adherence, invasion, apoptosis, prostaglandin synthesis and tissue pathology.

Immunohistochemical characterization of numerous histological sections of 3-D Int-407 tissue aggregates and Int-407 monolayers by fluorescent microscopy were consistent with the degree of differentiation between the two cultures. In general histological sections of the 3-D intestinal aggregates revealed tissue organization and differentiation similar to that found in vivo, while monolayer material showed poor organization, reduced expression of specific markers normally present in differentiated human intestinal epithelium, and reduced expression of the differentiated phenotype. The increased express by 3-D aggregates of extracellular and basement membrane proteins, specific epithelial and endothelial cell markers, and mucin, indicates important aspects of differentiated tissues, and suggests that the 3-D cell aggregates have the ability to organize and develop into complex tissue assemblies capable of expressing in vivo-like functional characteristics. The enhanced expression by 3-D aggregates of sialyl Lewis A suggests that the M-cell glycosylation pattern expressed on the surface of the 3-D Int-407 aggregates grown in the RWV may present an epithelial surface to the infecting microbe which more closely resembles that encountered within the host during infection, relative to the Int-407 monolayers. This finding is of particular relevance, since numerous pathogens in addition to *Salmonella* demonstrate a tropism for M cells. However, no continuous M cell line is currently available.

The expression of distinct glycoconjugates by normal human Peyer's patch M cells suggests an important role for carbohydrate epitopes in the function of this unique epithelial cell type. The structural modifications of the M-cell apical surface and the display of particular oligosaccharides together would allow M cells to present a conspicuously unique biochemical face to the lumen which might facilitate adherence, uptake, and immunological sampling of microorganisms. Expression of cytokeratin 18, a marker associated with tumor, abnormal and undifferentiated cells, was dramatically down-regulated in the 3-D aggregates as compared to monolayers. The decreased expression of cytokeratin 18, is suggestive of a shift from a relatively undifferentiated state (as in the monolayers) to the differentiated phenotype observed for the 3-D tissue aggregates. Histochemical staining with a periodate-Schiff (PAS) assay demonstrated that the 3-D constructs contained a mucousproducing sub-population of cells that expressed a differential phenotype compared to the surrounding cells. This differential staining pattern is very similar to that observed for mucous-secreting goblet cells within fixed, paraffin sections of intestinal tissue. In contrast to the 3-D aggregates, the monolayers did not produce a positive PAS reaction. The presence of a sub-population of PAS-positive cells in paraffin sections of the intestinal-derived Int-407 cell constructs is highly suggestive that culture of these cells in the bioreactor as three-dimensional, multi-cellular constructs results in the expression of differential cellular phenotypes, one of which apparently is a "mucous-producing" cell type and represents another important similarity to the intestinal mucosa.

Studies of the intestinal 3-D aggregates and monolayer cultures via whole mount confocal microscopy using proteins that serve as widely accepted markers of epithelial differentiation revealed a number of important distinctions between the two cultures conditions. While both culture types expressed epithelial specific antigen (ESA) and cadherin on the cell surfaces, the stratified epithelioid 3-D constructs express a much greater amount of these proteins. Furthermore, the proteins are localized specifically to cell-cell interfaces within the closely adherent cell layers of 3-D cultures. This finding indicates that the 3-D culture constructs have well-defined lateral cell-cell borders and junctional complexes throughout, while the monolayer cultures appear to possess nascent lateral polarity in a large proportion of the cell population.

In comparison to Int-407 cells grown as monolayers in culture, the expression of the basal lamina proteins Type IV collagen and laminin were dramatically upregulated in the 3-D cultures. During the development of polarity in the epithelial phenotype, the basal lamina is deposited at the cell-substrate interface of a nascent epithelium following the establishment of strong lateral polarity within the epithelium. In 3-D Int-407 cultures, which already possess well-established lateral polarity, the upregulated synthesis of basal laminal proteins is highly indicative of the first stages in the formation of apical-basal polarity. Furthermore, the deposition of these proteins at the cell-substrate interface, in this case the surface of the cytodex microcarrier beads, serves to convince us that the 3-D cultured cells are setting up apical-basal polarity by constructing a nascent basal lamina on their substrate.

Moreover, unlike their monolayer counterparts, analysis of Int-407 samples by TEM indicated that the 3-D intestinal aggregates exhibited well-formed and numerous microvilli at their apical cell surfaces, abundant and well-developed vacuolar-like formation, and extensive and well-formed tight junctions. In summary, the results of microscopy studies demonstrate that, based upon biochemical differentiation, cell polarity and cell ultrastructure, the 3-D Int-407 aggregates much more closely resemble human differentiated intestinal epithelium than do conventional monolayer cultures of the same cells. As such, 3-D Int-407 cultures would be predicted to more closely replicate the complex environment encountered by *Salmonella* or other pathogen during the natural course of human infection.

Results from infectivity studies demonstrated that *Salmonella* established infection of the 3-D human intestinal cells in a much different manner as compared to monolayer cultures. *Salmonella* exhibited significantly reduced abilities to adhere to and invade the 3-D human intestinal aggregates as compared to monolayer cultures. In agreement with this finding SEM analysis of *Salmonella*-infected intestinal cells revealed fewer bacteria associated with the surface of the 3-D aggregates as compared to monolayers following time-course infections. This may be a reflection of the differential expression of host cell surface adhesions by the 3-D Int-407 cells which are more relevant to the in vivo setting as compared to growth as monolayers. Although *Salmonella* adhered to and invaded the 3-D intestinal cells poorly, these cells did exhibit signs of *Salmonella* induced-damage at later post-infection time points. The question arises as to how *Salmonella* is able to induce damage to the host epithelium if it adheres and invades poorly to this tissue. In vitro studies have shown that the Type III secretion system encoded on *Salmonella* Pathogenicity Island I is required for the translocation of proteins into host epithelial cells and the induction of fluid secretion, and inflammatory responses. Given the inherent differences in the structural modifications of the surfaces of the 3-D intestinal epithelial cells as compared to monolayers, it is possible that the secretion of Type III effector proteins is induced in a different manner in the 3-D aggregates following *Salmonella* infection.

Both in vitro and in vivo studies have shown that interaction of wild-type virulent serovar *Typhimurium* with intestinal epithelium induces a number of morphological changes to the host epithelium important for subsequent bacterial invasion. These changes include, cytoskeletal rearrangement with the formation of membrane ruffles upon the site of *Salmonella* contact, blunting and transient denuding/degeneration of microvilli from enterocytes, destruction of M cells, and the formation of pathological lesions. 3-D Int-407 aggregates displayed minimal change in overall morphology following *Salmonella* infection as compared to the extensive loss of integrity observed for Int-407 monolayers following the same time course of infection. Since the 3-D aggregates more closely resemble human intestinal epithelium, the difference in structural integrity following *Salmonella* infection of these tissues as compared to monolayers is more reflective of an in vivo infection.

Induction of tissue damage in the form of apoptosis is a common response of host tissues to infection with bacterial pathogens. Several mediators produced in response to *Salmonella* infection, such as TNF-α, also have the potential to induce apoptosis of epithelial cells. Not surprisingly, *Salmonella* species have been shown to induce apoptosis following infection of several cell types, including cultured macrophage and a human colonic epithelial cell line. However, the onset of cell apoptosis in each of these cell types following *Salmonella* infection was dramatically different, with a rapid onset of apoptosis (within 2 hours) following infection of macrophage and a delay of up to 12–18 hours following bacterial entry into colon epithelial cell lines. The percentage of apoptosis in Int-407 cells grown as monolayers was significantly increased 90 minutes post-infection with *Salmonella* as compared to uninfected controls. There was a rapid onset of apoptosis following *Salmonella* infection of Int-407 monolayers, with between a 70%–90% apoptotic index occurring 90 minutes after infection. However, there was no difference in apoptosis between infected and uninfected 3-D Int-407 tissue aggregates at the same time post-infection. In addition, the results from adherence and invasion studies also support these observations, as *Salmonella* adherence to and invasion into 3-D Int-407 aggregates was significantly less than that observed for Int-407 monolayers. Considering that the vast majority of cases of *Salmonella*-induced gastroenteritis go unreported, (less than 5%), it seems unlikely that following ingestion of *Salmonella*, approximately 70% of human intestinal epithelial cells undergo apoptotic death. Thus, the lower levels of apoptosis observed following *Salmonella* infection of 3-D human intestinal aggregates would likely be more reflective of an in vivo infection.

The present invention discloses the use of three-dimensional tissue aggregates cultured in the RWV as a model for microbial infectivity by a bacterial pathogen. The bacterium used in these studies, *Salmonella enterica* serovar *Typhimurium*, belongs to the family Enterobacteriaceae, a larger group of Gram negative rods whose natural habitat is the intestinal tract of humans and animals, and which includes most of the bacteria that cause intestinal and diarrheal disease, considered to be one of the greatest health problems globally. However, it should be noted that there are many bacterial pathogens which gain access to animal hosts in a manner similar to *Salmonella*, i.e., by attaching to and invading the gut-associated lymphoid tissue (GALT) and then disseminating to visceral lymphoid tissues to cause systemic disease. These bacteria include many other enteric pathogens, such as *Shigella* and enteropathogenic *E. coli*, including the 0157:H7 type, as well as other microbial pathogens such as *Listeria monocytogenes*. Thus, the use of 3-D tissue aggregates of human intestinal cells will have broad applicability and therefore significance in detailing how microbial pathogens which are invasive through the GALT gain access to and establish infection within the host.

Figure 2:
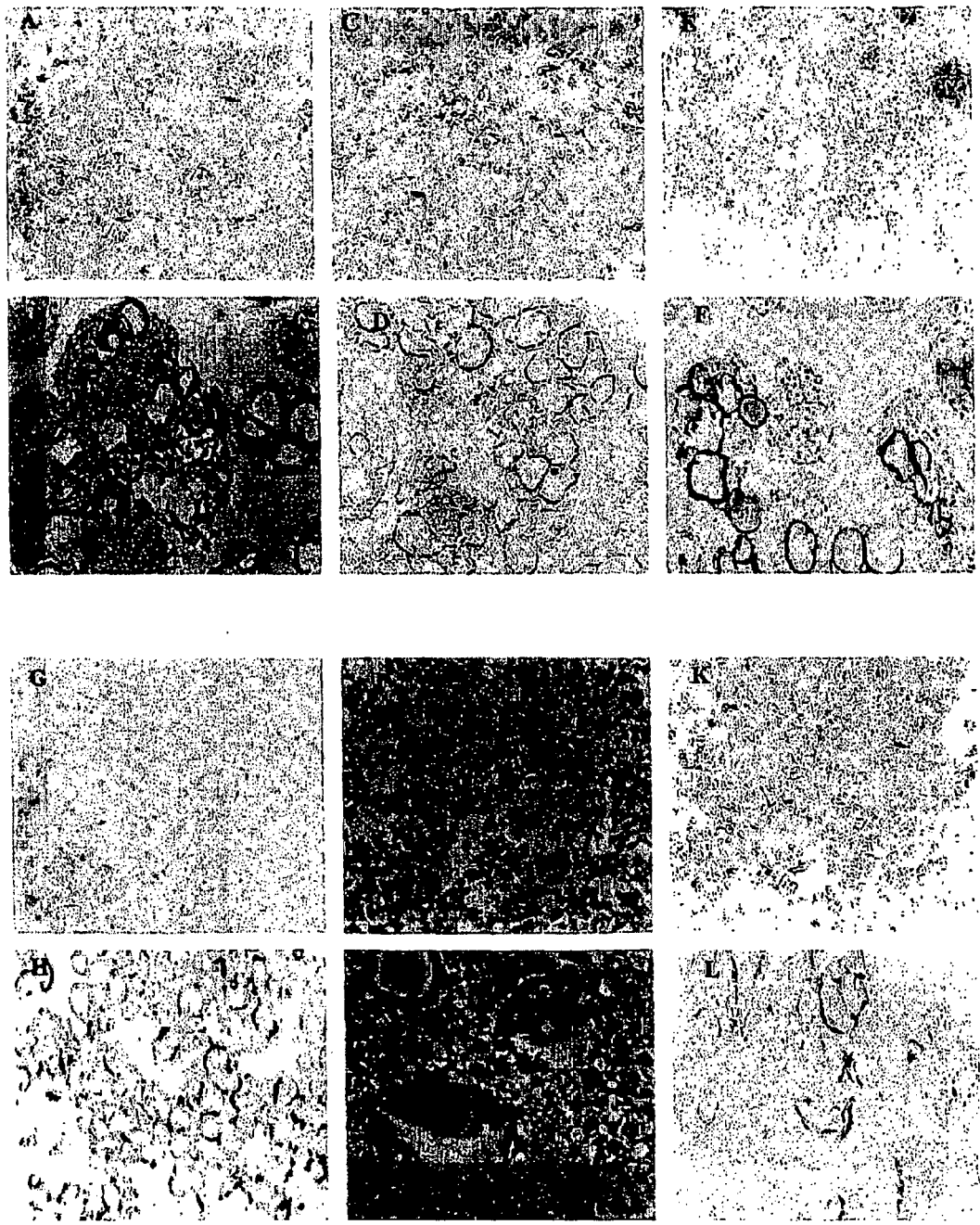
FIG. 2 shows the immunohistochemical analysis of 3-D Int-407 aggregates as compared to Int-407 monolayers. This figure demonstrates positive staining in 3-D Int-407 tissue aggregates for collagen type II, fibronectin, sialyl Lewis A, and villin (B, D, F, and H, respectively) (100×), and the absence of staining for cytokeratin 18 (J) as compared to Int-407 monolayers stained for the same markers (A, C, E, G, and I, respectively) (100×). Antibody negative controls for 3-D tissue aggregates and monolayers (K and L, respectively), (100×), demonstrate total lack of staining. For reference, circular and oval lumenal areas seen in the photos are cross sections of microcarrier spheres around which cellular material is growing.
Figure 3:
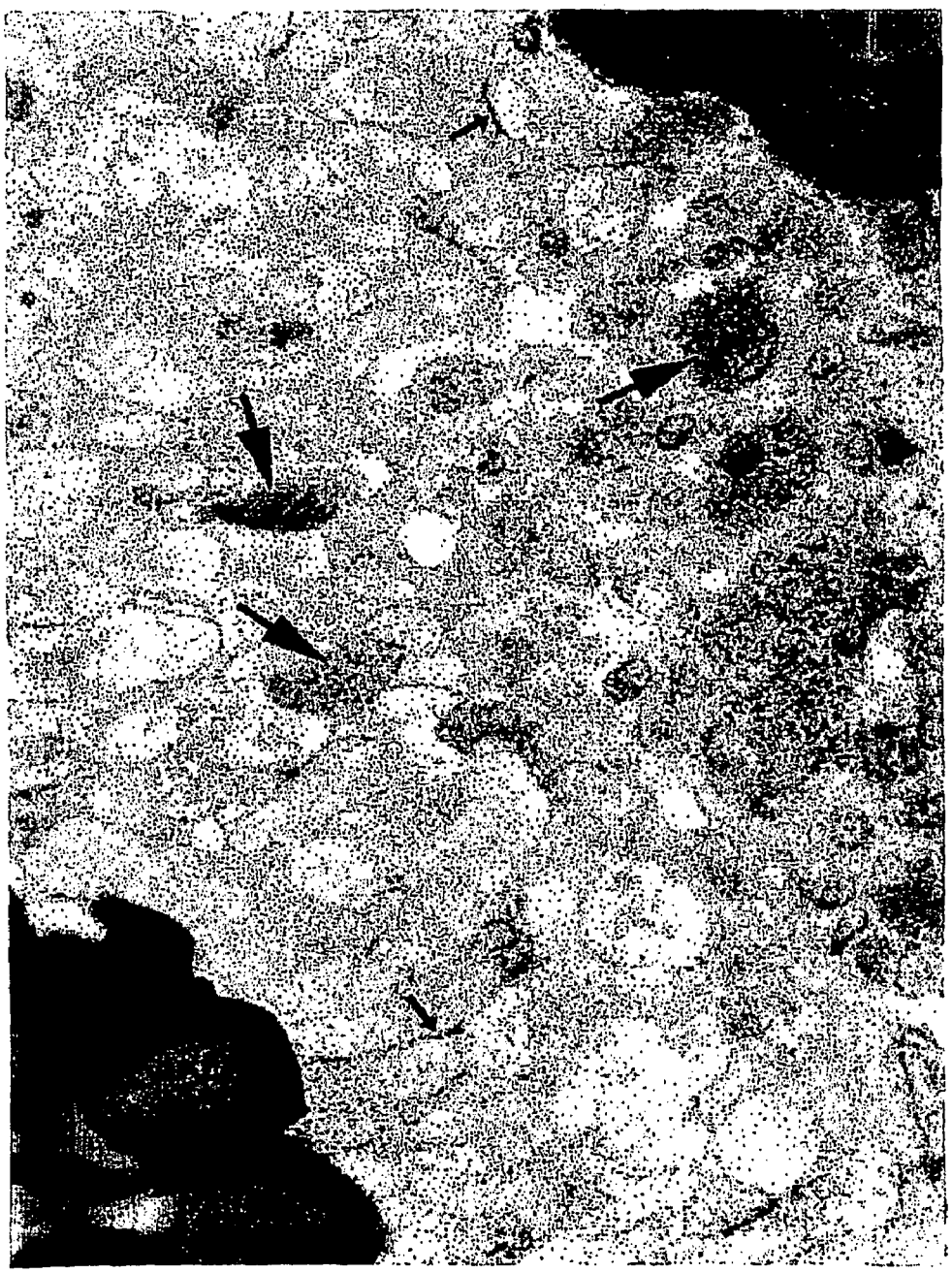
FIG. 3 shows the periodic acid-Schiff (PAS) Staining of paraffin sections of Int-407 3-D constructs. The figure shows the presence of isolated PAS-positive cells (large arrowheads) surrounded by PAS-negative cells. Cytodex beads (*) and some discrete areas of extracellular matrix (small arrows) also exhibit a positive reaction with the PAS stain. The presence of a differential PAS staining pattern in paraffin sections of 3D constructs suggests the presence of a mucous-producing sub-population of cells within the construct.

Characterization of the in vivo epithelial cell expression characteristics of the RWV-grown intestinal 3-D aggregates relative to monolayer cultures was determined by examining immunohistochemical and proto-oncogene expression patterns of histological sections of these cultured cells. Immunohistochemical analysis was performed on histological sections of tissue obtained from the RWV and monolayer controls with antibodies against collagen II and III, fibronectin, vimentin, pancytokeratin, von Willebrand factor, sialyl Lewis A, villin, and cytokeratin 18. Immunohistochemical analysis of 3-D Int-407 aggregates as compared to monolayers revealed striking differences between the two cultures. In general, the 3-D intestinal aggregates demonstrated tissue organization similar to that found in vivo (FIGS. 1C and 1A, respectively), while monolayer material showed poor organization (FIG. 1B), reduced expression of specific markers normally present in differentiated human intestinal epithelium, and reduced expression of the differentiated phenotype. Specifically, 3-D aggregates of Int-407 cells exhibited very strong staining for the extracellular matrix proteins collagen type II (FIG. 2B) and fibronectin (FIG. 2D), as compared to weakly to moderately positive staining for these same epitopes in Int-407 Monolayers (FIGS. 2A and C, respectively). In addition, expression of the M-cell glycoconjugate sialyl Lewis A antigen was also enhanced in the 3-D aggregates (FIG. 2F) relative to the monolayers (FIG. 2E). Three-dimensional aggregates also exhibited increased staining for the cytoskeletal marker villin (an abundant protein in the brush border epithelial cells of the small intestine) (FIG. 2H), as compared to the weaker staining for this epitope observed in Int-407 monolayers (FIG. 2G). Expression of cytokeratin 18, a marker associated with tumor, abnormal and undifferentiated cells, was dramatically down-regulated in the 3-D aggregates (FIG. 2J) as compared to monolayers (FIG. 2L). Moreover, the 3-D aggregates also exhibited enhanced staining for von Willebrand factor (endothelial cell marker), collagen III, vimentin, and pancytokeratin as compared to monolayers (data now shown). Negative controls for all immunohistochemical analyses are shown in FIGS. 2K (monolayers) and 2L (3-D aggregates), respectively. In addition, histochemical staining with a periodate-Schiff (PAS) assay showed mucins to be produced by the 3-D Int-407 aggregates (FIG. 3), but not by monolayers (data not shown).

Figure 4:
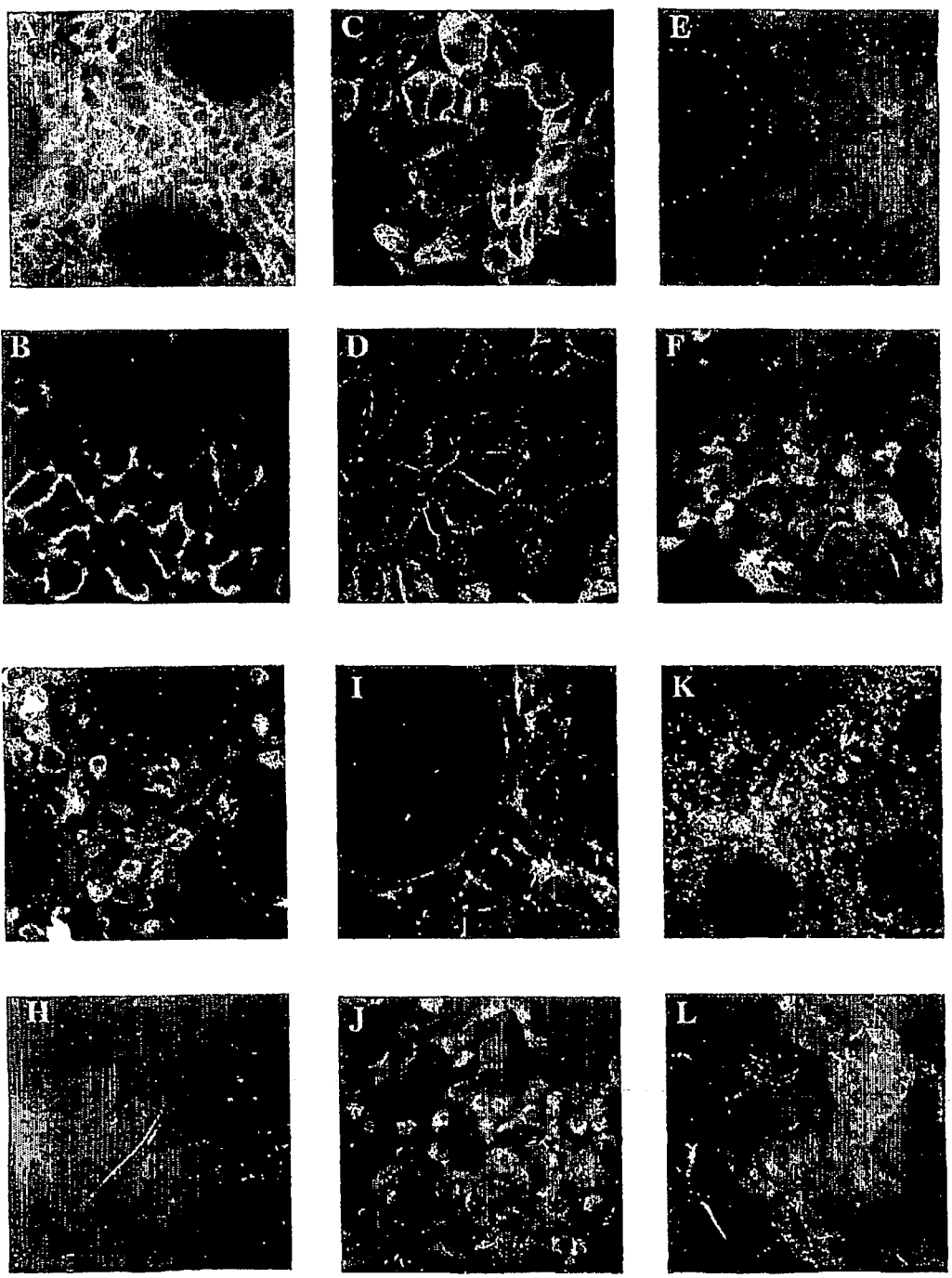
FIG. 4 shows confocal images of antibody stained Int-407 monolayers and 3-D constructs. Confocal images of Int-407 cells grown as monolayers (B, D, F, H, J, and L) and 3-D aggregates (A, C, E, G, I, and K) stained with monoclonal antibodies against epithelial specific antigen (ESA) (A-B), cadherin (C-D), cytokeratin 19 (E-F, note the 150 μm beads are delineated by a dotted outline in G), laminin (I-J), and collagen type IV (K-L).

Characterization of the in vivo epithelial cell expression characteristics of the intestinal 3-D aggregates relative to monolayer cultures was further studied via immunohistochemical analysis by whole mount confocal microscopy of tissue obtained from the bioreactor and monolayer controls with antibodies against type IV collagen, laminin, cadherin, epithelial specific antigen (ESA) and cytokeratin 7, all of which are proteins that serve as widely accepted markers of epithelial differentiation. Immunostaining for epithelial specific antigen (ESA), an antigen expressed only in epithelia, indicated that the Int-407 cells were epithelial in nature. All cells in both the monolayer cultures and in the 3-D epithelial constructs expressed this antigen (FIGS. 4B and A, respectively). Confocal microscopy of the cell surface ESA showed how densely populated the interstices of the stratified epithelioid 3-D constructs were with closely adherent layers of cells, in contrast to that seen in monolayer culture (FIGS. 4A and B, respectively).

As epithelia form, the cells adhere to each other via lateral cell-cell interactions mediated by a class of plasmalemmal binding proteins known as the cadherins. Developmentally mature epithelia display a very tight association of cadherins to their lateral surfaces in the areas where they adhere to other cells. Ultrastructurally, this zonulae adherens is easily identified as a band of actin filaments decorated with dense accumulations of cadherin protein. The 3-D Int-407 cultures showed just such a dense, regular appearance of the cadherin assemblies along their lateral cell-cell boundaries (FIG. 4C). By comparison, the monolayer cultures displayed copious cadherin accumulations only in areas containing closely proximated cells, areas that occur with much less frequency (FIG. 4D). This indicated that the 3-D culture constructs have very well-defined lateral cell-cell borders and junctional complexes throughout, while the monolayer cultures appear to still be in the process of initiating lateral polarity in a large proportion of the cell population.

In comparison to Int-407 cells grown as monolayers in culture, the expression of laminin (FIGS. 4I–J) and Type IV collagen (FIGS. 4K–L) were dramatically upregulated. Both of these proteins are known to contribute to formation of the basal lamina, a structural component of all developmentally mature and fully functional epithelia. Developmentally, the basal lamina is deposited at the cell-substrate interface of a nascent epithelium defined only by lateral cell-cell adhesions, thus imparting an apical-basal polarity to the entire structure. In 3-D Int-407 cultures, the presence of these basal laminal proteins, and their deposition at the cell-substratum interface, is highly indicative of the first stages in the formation of apical-basal polarity (FIGS. 4I and K, respectively).

The expression and histological pattern of a group of cytoskeletal proteins, the cytokeratins, was studies. Cytokeratin 19, a marker associated with tumor and abnormal cells, was dramatically down-regulated in the 3-D aggregates (FIG. 4E) (note: 150 μm beads are delineated by a dotted outline) as compared to monolayers (FIG. 4F). Conversely, cytokeratin 7, absente in the monolayer cultures (FIG. 4H) was upregulated by 3-D culture conditions (FIG. 4G). The modulation of cytokeratin is indicative of large-scale phenotypical alterations associated with 3-D culture.

Figure 5:
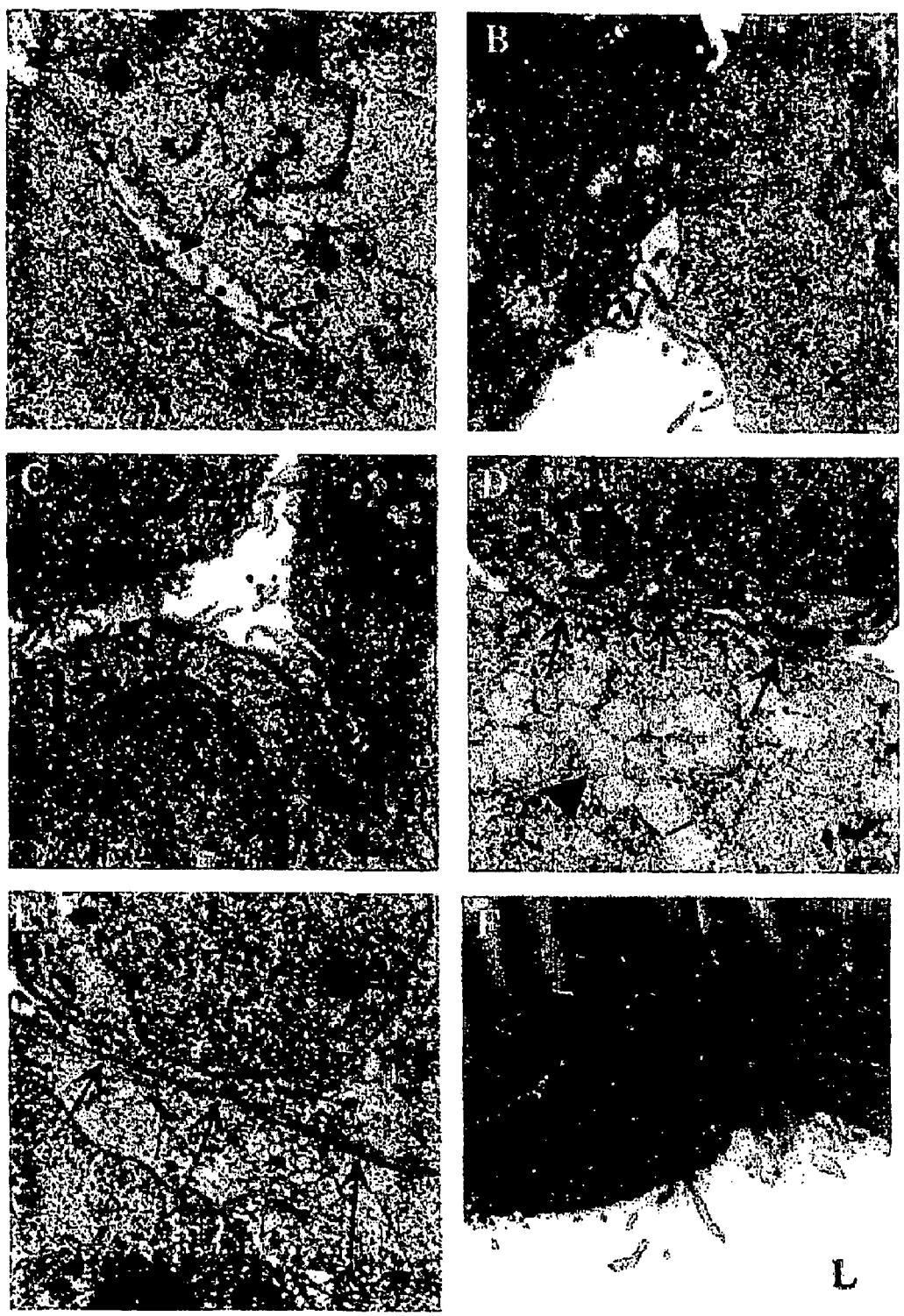
FIG. 5 shows transmission electron micrographs (TEM) of 3-D Int-407 aggregates as compared to Int-407 monolayers. This figure demonstrates TEM images of Int-407 monolayers (A-B) and 3-D Int-407 cells (C-F). The microvilli observed in the monolayers (A) are poorly developed and sparse in number compared to the well-developed and abundant microvilli in the 3-D aggregates (L) (solid arrows). In addition, the monolayers show high levels of cellular granularity (Panel B.*) indicative of poorly differentiated cells. Moreover, the monolayers (A-B) demonstrate inferior tight junction formation as compared to the 3-D aggregates (D-E) (concave arrows). Panel E shows the formation of tight junctions which nearly run the length of the margin between two 3-D cells (concave arrows). Note the presence of numerous, well-formed vacuolar-like structures in the 3-D aggregates (D) as compared to their poorly developed counterparts in the monolayers (B) (arrow heads). In Panel F, two cytodex microcarrier beads (b) can be seen which are partially covered with 3-D cells. The microvilli display an apical orientation toward the luminal (L) side.
Figure 6:
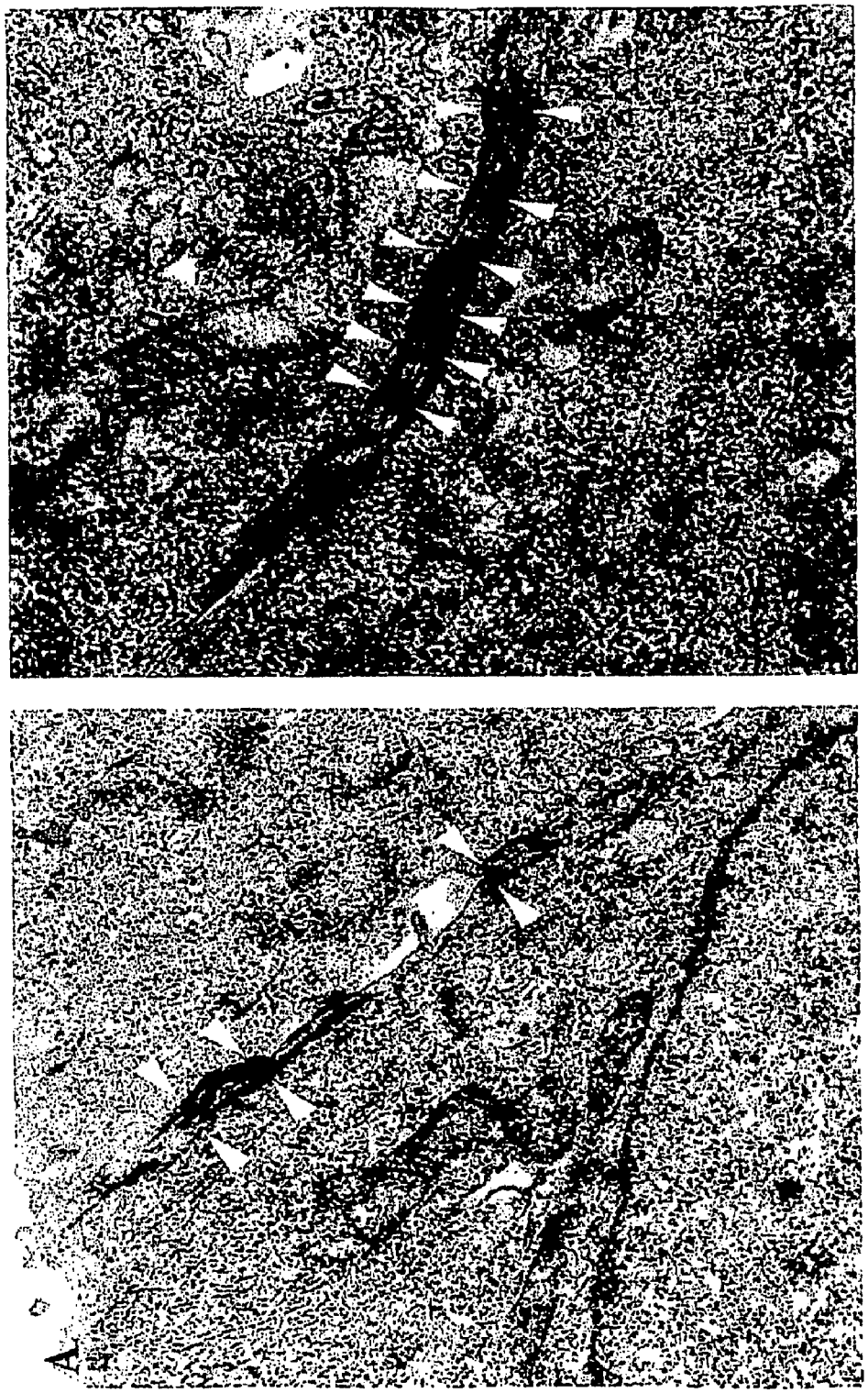
FIG. 6 shows transmission electron micrographs of desmosome formation in the 3-D Int-407 aggregates (B) compared to Int-407 monolayers (A). The desmosomes in the monolayer are poorly formed and incomplete.

Characterization of the in vivo epithelial cell expression characteristics of the 3-D intestinal aggregates relative to monolayer cultures was further examined using TEM analysis. Overall, monolayer cultures demonstrated poor structural and functional fidelity as compared to their 3-D counterparts. Specifically, monolayer cultures exhibited irregular microvilli development (FIG. 5A), significant cellular granularity (FIG. 5B) accompanied by minimal tight junction formation (FIGS. 5A, B), poorly formed gladular/vacuolar-like formation (FIG. 5B), and lack of apical polarity. In contrast, 3-D cultures demonstrated well-developed and abundant microvilli (FIG. 5C) which were apically oriented (FIG. 5F), well-formed tight junctions (FIGS. 5D, E), and numerous, well-formed vacuolar-like structures (FIG. 5D).

An initial step in the pathogenesis of *Salmonella* infection is the adherence and entry of these organisms into the intestinal epithelium. Accordingly, the ability of serovar Typhimurium χ3339 to adhere to and invade 3-D tissue aggregates of Int-407 cells was examined, as compared to Int-407 monolayers. Representative data from three trials showed that, with respect to the percentage of initial inoculum (MOI 10:1), the adherence and invasion of *Salmonella* into 3-D Int-407 cells (2.6±1.3 and 1.3±0.8, respectively) was significantly lower than that observed for Int-407 monolayers (48.0±19.0, and 51.0±18.0, respectively).

Figure 7:
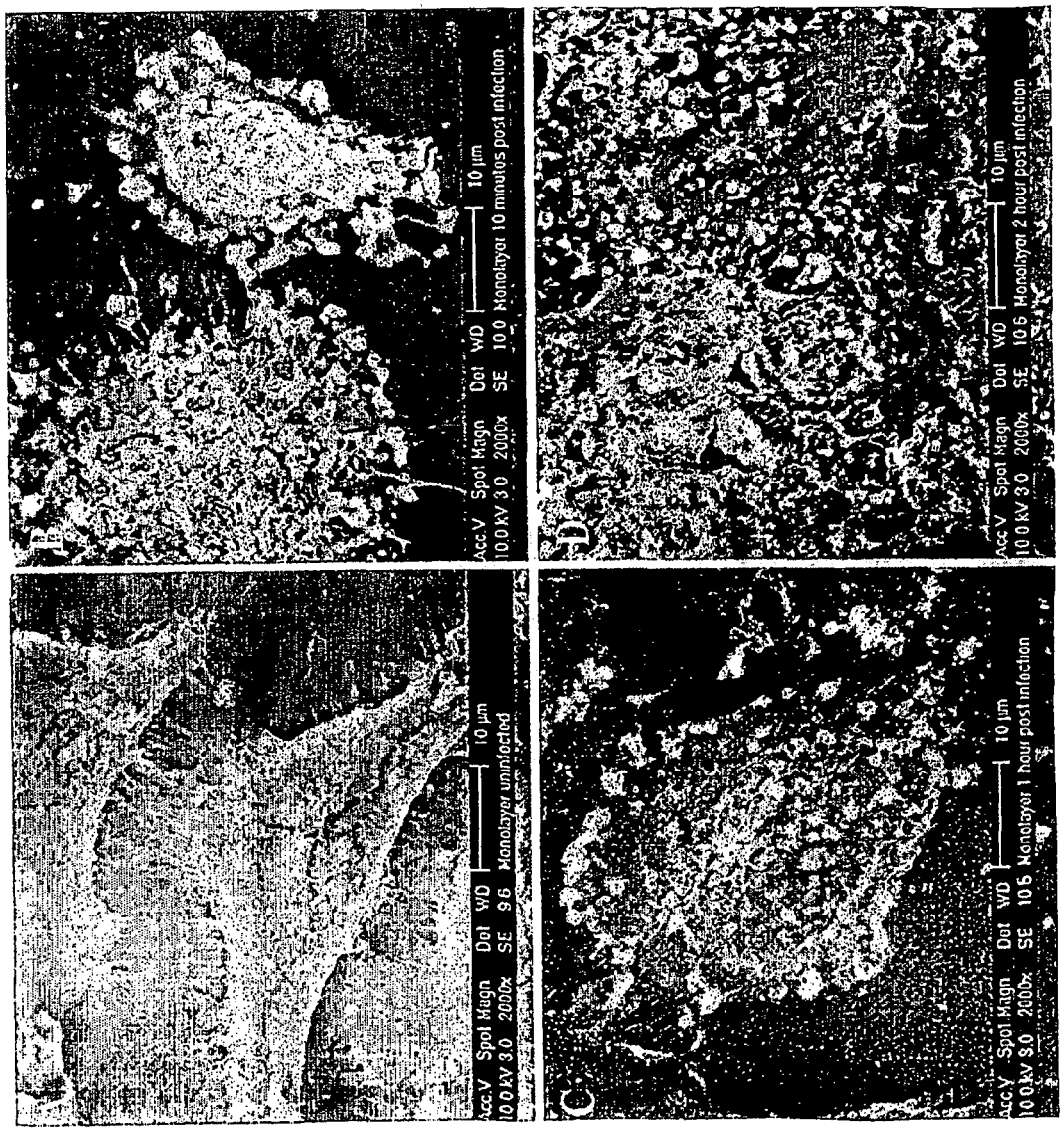
FIG. 7 shows scanning electron micrographs (SEM) of *Salmonella* with Int-407 monolayers. Electron micrographs of uninfected and infected Int-407 monolayers are at 2,000× magnification. Uninfected monolayer control (A); monolayer at 10 minutes post-infection, (at an MOI of 10:1), showing dramatic surface alterations, including extensive formation of membrane blebs and several surface structures resembling ruffles (B); by 1 hour post-infection, the Int-407 cell surface appears swollen and denuded with membrane blebs (C); at 2 hours post-infection, Int-407 cells exhibit loss of structural integrity with numerous membrane alterations including blebs and the formation of pathological lesions, as well as some surface bound bacteria (D)).

Pathology of 3-D tissue aggregates relative to monolayers before and after infection with *Salmonella*. Scanning electron microscopy (SEM) was used to examine surface interactions and membrane structural alterations which occurred over time following *Salmonella* infection of 3-D Int-407 aggregates as compared to monolayers. Observations of numerous samples revealed major changes in the integrity of the monolayers as compared to 3-D intestinal tissues following time-course infections with *Salmonella* at the same MOI. At time zero, SEM revealed typical, young confluent monolayers (FIG. 7A). As early as 10 minutes post-infection, observable differences in structural integrity were observed in the Int-407 monolayers as compared to uninfected controls, the former showing extensive formation of membrane blebs, and several areas of protruding cytoplasm resembling membrane ruffles (FIG. 7B). One hour postinfection, the Int-407 monolayers appeared swollen with membrane blebs and the formation of pathological lesions (FIG. 7C). There was a dramatic loss of structural integrity of the monolayers at 2 h post-infection, including the presence of extensive lesions, as well as large swollen areas of denuded surface membrane (FIG. 7D).

Figure 8:
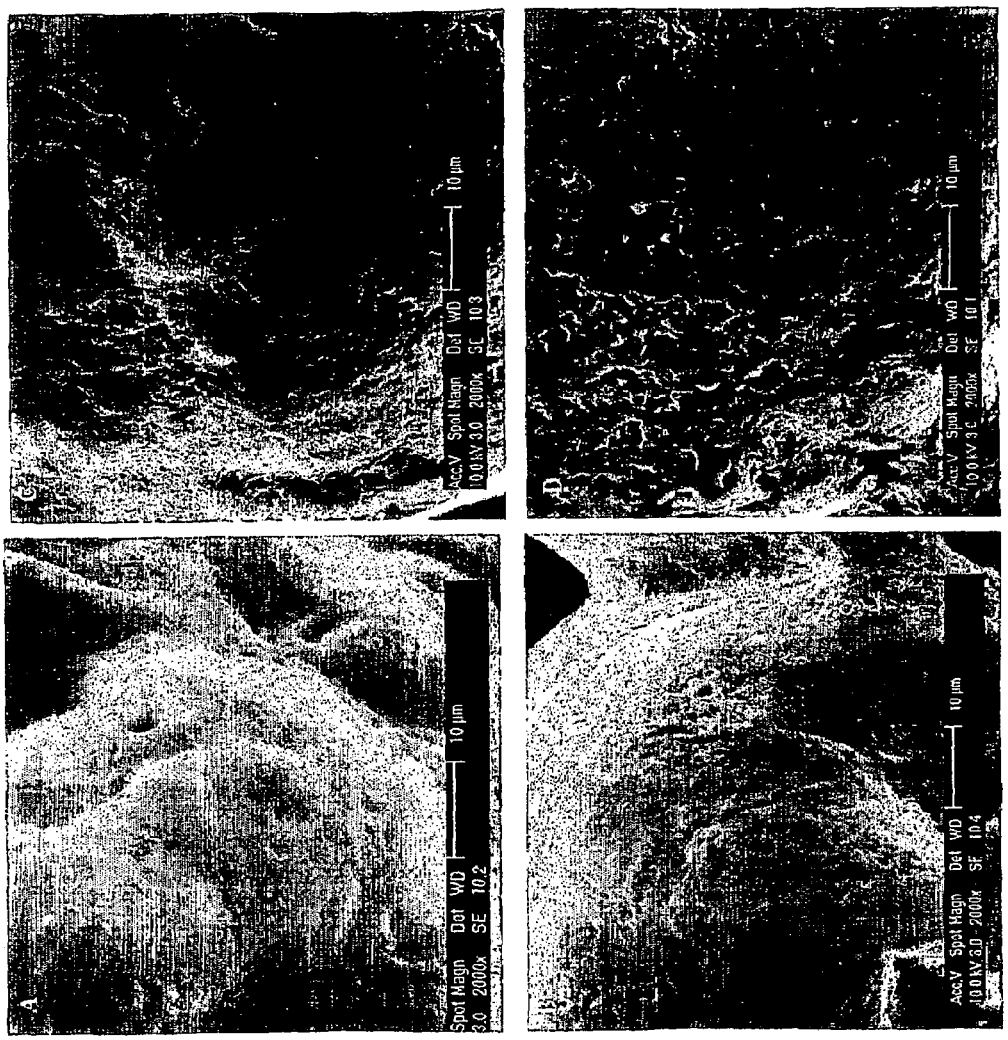
FIG. 8 shows scanning electron micrographs of uninfected and infected 3-D Int-407 aggregates. Electron micrographs of uninfected and infected 3-D Int-407 aggregates in the HARV are at 2,000× magnification. Uninfected 3-D Int-407 control showing dense masses of cells with extracellular secretions (A); 3-D Int-407 aggregates at 10 minutes post-infection (at an MOI of 10:1), showing minor irritation on the Int-407 apical cell membrane (B); by 1 hour post-infection, numerous surface depressions and/or membrane blebs are apparent on the 3-D Int-407 cells, with depressed regions devoid of mucous-like secretions (C); at 2 hours post-infection, the surface of the 3-D Int-407 cells is quite irregular and associated with what appear to be numerous surface lesions (D). Few surface bound bacteria were observed at any of the above postinfection times.

Three-dimensional Int-407 tissue aggregates infected with *Salmonella* did not display as extensive loss of structural integrity as observed for infected Int-407 monolayers following the same time-course of infection. At time zero (i.e. uninfected control), SEM revealed dense masses of cells associated with the microcarrier beads with apparent mucous-like extracellular secretions covering the cells. Note the "furry" appearance of what appear to be microvilli present on the epithelial cell aggregates (FIG. 8A). Ten min post-infection, the surface of the 3-D Int-407 cells appears slightly irritated, however, unlike the infected monolayers, few bacteria are observed in association with the surface of the 3-D aggregates (FIG. 8B). One hour post-infection, numerous depressed/pitted areas are evident, which are devoid of mucous-like extracellular secretions (FIG. 8C). By two hours post-infection, numerous lesions are apparent on the surface of the 3-D Int-407 cells. In addition, regions of membrane blebbing are also abundant (FIG. 8D).

Figure 9:
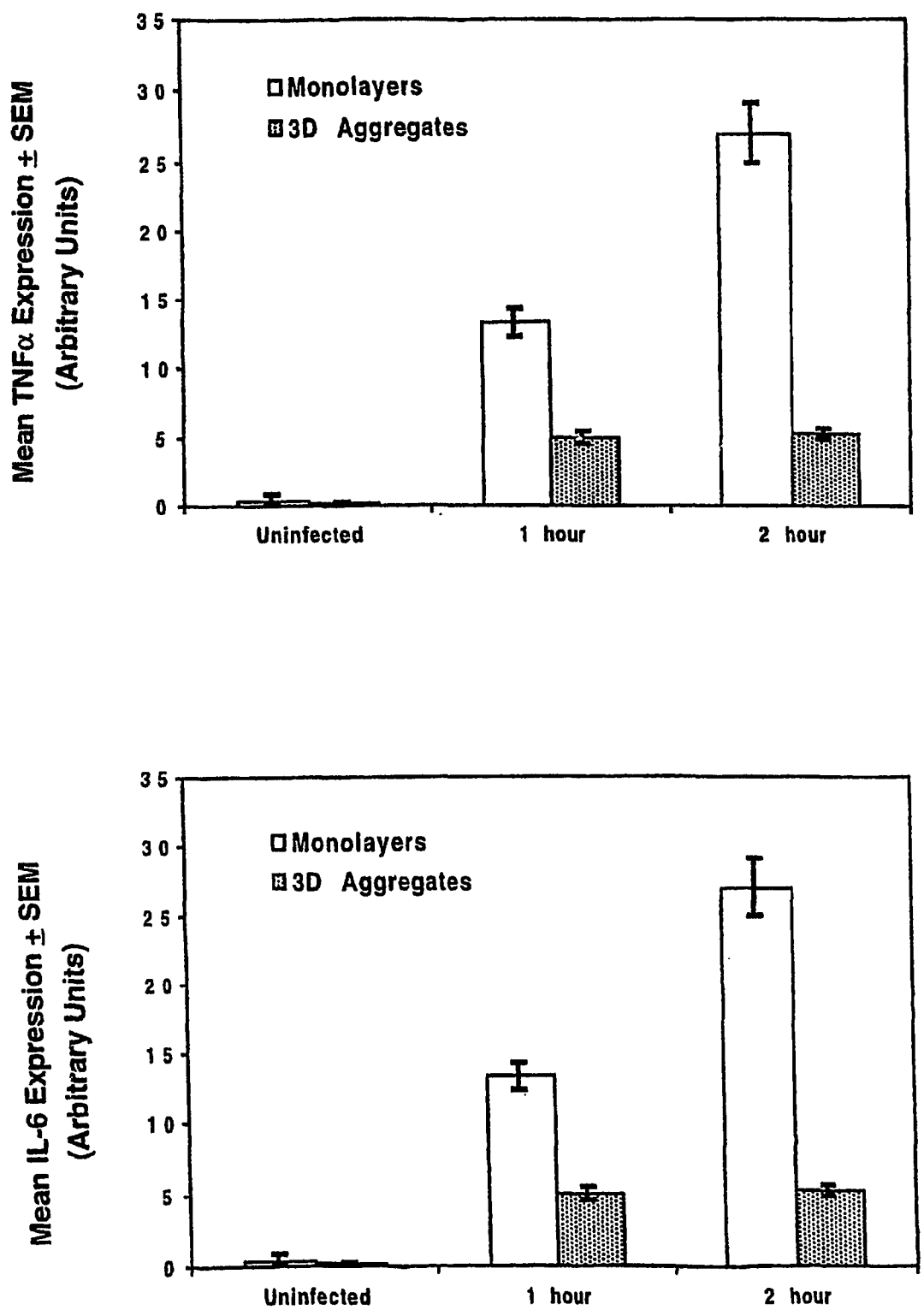
FIG. 9 shows cytokine expression of Int-407 monolayers and 3-D tissue aggregates following *Salmonella* infection. Total RNA was isolated from Int-407 monolayers and 3-D tissue aggregates prior to infection with *Salmonella* and at 1 h and 2 h after infection. Five jig total RNA from each sample was hybridized individually with radiolabeled riboprobes specific for TNFα (Panel A) or IL-6 (Panel B) and subjected to RNAse protection. Phosphorimager technology was used to quantify the levels of transcription of each cytokine and the housekeeping gene, GAPDH. Levels of TNFα and IL-6 transcripts were normalized using GAPDH transcription levels of the same RNA sample and the levels are displayed as arbitrary units.

In order to characterize the cytokine expression of 3-D Int-407 aggregates as compared to monolayer cultures following infection with serovar Typhimurium, a commercially available multiprobe RNAse protection assay was used to quantify and compare the cytokine mRNA profiles. Infection of both Int-407 monolayers and 3-D aggregates with serovar Typhirnurium resulted in significantly increased expression of TNFα, IL-6, IL-1α, IL-1β and IL-1RA at 1 hour and 2 hours after infection compared to uninfected monolayers and 3-D aggregates, respectively. Representative data are shown for TNFα (FIG. 9A) and IL-6 (FIG. 9B). Infection of INT-407 monolayers with *Salmonella* induced significantly increased expression of TNFα at one hour after infection (P<0.0005) and at 2 hours after infection (P<0.0001) compared to uninfected monolayers (FIG. 9A). TNFα mRNA levels were significantly elevated at one hour (P<0.0005) and 2 hours (P<0.0001) after infection of 3-D aggregates compared to uninfected 3-D aggregates, however, TNFα expression did not increase from one hour after infection to two hours after infection (FIG. 9A). Although, infection of both Int-407 monolayers and 3-D aggregates resulted in increased TNFα mRNA levels. TNFα expression was more than five-fold higher in the monolayers at two hours after infection compared to the 3-D aggregates. Similarly, infection with serovar *Typhimurium* induced expression of IL-6 in both Int-407 monolayers and 3-D aggregates (FIG. 9B). Significantly higher levels of IL-6 mRNA were detected at one hour (P<0.002) and two hours (P<0.0001) after infection of Int-407 monolayers compared to uninfected monolayers. Infection of Int-407 monolayers resulted in greater than a 50-fold increase in IL-6 transcription at two hours after infection compared to uninfected monolayers (FIG. 9B). Although IL-6 transcription in Int-407 3-D aggregates was significantly higher at two hours after infection (P<0.005) compared to uninfected 3-D aggregates, the overall increase was just over three-fold in magnitude.

Transcription of IL-1α. IL-1β and IL-1Ra was also elevated following infection of Int-407 monolayers and 3-D aggregates (data not shown). In each case, constitutive expression was higher in uninfected 3-D aggregates compared to monolayers. By two hours after infection of monolayers, IL-11 expression increased by 17-fold compared to uninfected monolayers and IL-1β expression increased by 13-fold; whereas, express of the IL-1 inhibitor, IL-1Ra, increased by just over three-fold. In contrast, two hours after infection of 3-D aggregates, IL-1α expression increased four-fold and IL-1β expression increased approximately three-fold while expression of IL-1Ra was increased two-fold compared to uninfected 3-D aggregates. Taken together, it appears that IL-1α and IL-1β expression is upregulated more in Int-407 monolayers compared to 3-D aggregates; whereas, expression of the IL-1 inhibitor, IL-1Ra, is increased about the same in monolayers compared to 3-D aggregates following infection with serovar *Typhimurium*. Thus, proinflammatory effects of IL-1α and IL-1β may be more prominent in the Int-407 monolayers following infection with serovar *Typhimurium* as compared to the 3-D aggregates.

TGF-β1 frequently serves in an immunosuppressive role, and therefore, the expression of this cytokine following infection of Int-407 monolayers and 3-D aggregates was examined. Although, infection with serovar *Typhimurium* did not significantly affect expression of TGF-β1 at one or two hours after infection of either monolayers or 3-D aggregates, TFG-β1 mRNA levels were always two-fold higher in the 3-D aggregates compared to the monolayers. Assay for apoptosis of human intestinal epithelial cells after *Salmonella* infection. When grown as monolayers, several cell lines have been shown to undergo apoptosis following *Salmonella* infection. To assess the relationship between bacterial infectivity and death of human intestinal Int-407 cells cultured in the RWV or as monolayers, flow cytofluorometry was used to characterize apoptotic cell death of these cells before and after *Salmonella* infection. Following 1.5 hours infection with *Salmonella*. Int-407 monolayers contained approximately eightfold more apoptotic cells (68.3%) than control uninfected monolayers (8.8%). In contrast, there was no increase in apoptosis following the same time course of *Salmonella* infection of 3-D Int-407 aggregates, with a 5.2% and 7.3% apoptotic index of aggregates pre and post-infection, respectively.

To determine whether there was a differential induction of prostagladin synthesis in response to *Salmonella* infection between the Int-407 cells cultured as 3-D aggregates or as monolayers, $PGE_2$ levels in these cells was measured by immunoassay before and after infection with χ3339 Levels of $PGE_2$ were not increased in 3-D Int-407 cells or in monolayers following *Salmonella* infection at 1, 2 or 8 h (Table 1). In contrast, there was a dramatic increase in the level of constitutive $PGE_2$ synthesis (approx. 79×) in the uninfected 3-D Int-407 cells as compared to the monolayer cultures (Table 1).

TABLE 1

$PGE_2$ production by Int-407 cells before and after infection with Salmonella[1]

| Culture | Control | $PGE_2$ produced (ng/ml) | | |
| --- | --- | --- | --- | --- |
| | | 1 hour | 2 hours | 8 hours |
| Int-407 Monolayers | 237.1 ± 16.2 | 349.3 ± 84.7 | 180.6 ± 18.6 | 162.9 ± 124.0 |
| 3-D Int-407 Cells | 18,724.3 ± 1.590 | 16.985 ± 1,240.0 | 14,142.9 ± 2,280 | 16,772.0 ± 73.6 |

[1]Time course of $PGE_2$ levels before and after Salmonella infection of 3-D Int-407 cells and Int-407 monolayers. Monolayers of Int-407 cells in 24 well plates, or 3-D Int-407 cells cultured in 24 well plates, were infected for 1 hour with serovar Typhimurium χ3339 at an MOI of approximately 50:1. After 1 h, cultures were further incubated with gentamicin (10 μg/ml) for another 7 hours. At the indicated times after infection, culture supernatant was collected and analyzed for $PGE_2$ by enzyme immunoassay.

Figure 10:
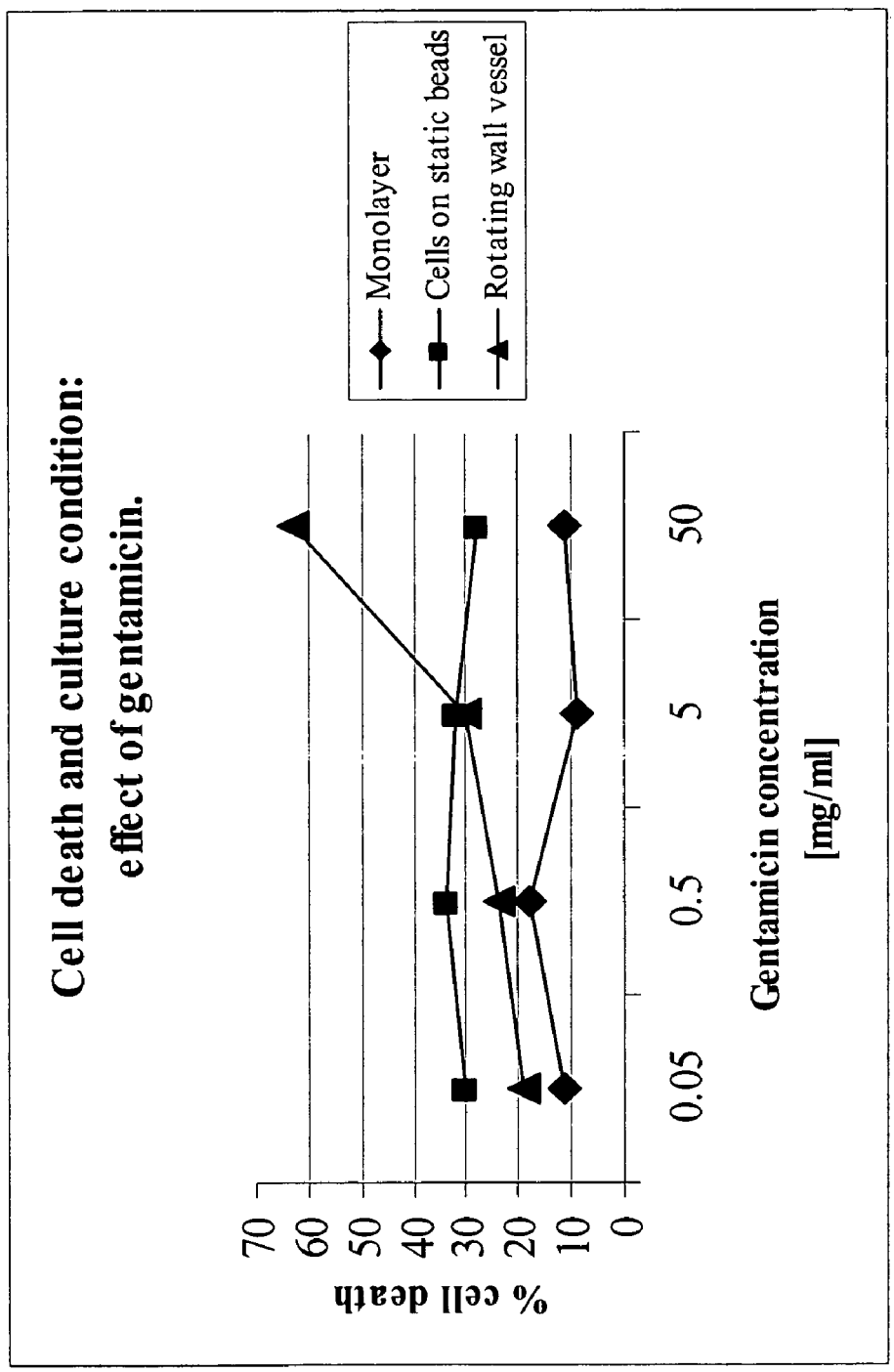
FIG. 10 shows that cell cultures in a rotating wall vessel exhibit a change in sensitivity to drugs and toxins. Immortalized human renal cells were cultured for 24 hours in either a monolayer (diamonds), as 3D cultures in a bag with beads for support (squares), or as 3D cultures in a rotating wall vessel (triangles), and treated with 0.05, 0.5, 5 or 50 mg/ml throughout the time period of the culture.

In order to compare the chemosensitivity of cells in a monolayer relative to those in a 3D aggregate either under static conditions, or falling at terminal velocity with applied shear, immortalized human renal cells were cultured in DMEM/F12 medium with 10% calf serum for 24 hours in either a Monolayer, a conventional cell bag culture or a rotating wall vessel. In separate aliquots of cells in separate vessels, gentamicin was added throughout the time period of culture at concentrations of 0.05, 0.5, 5 or 50 mg/ml. The cells in all cultures were then treated with gentamicin for six hours and the number of apoptotic and necrotic cells were counted using a flow cytometry assay. FIG. 10 depicts one data set for this experiment in which the monolayer is depicted as diamonds, the 3-dimensional cultures grown on beads in a bag are depicted as squares, and the 3-dimensional cultures in the rotating wall vessel are depicted as triangles. As judged by Kogomorov-Smirnoff summation statistics, renal cell growth on beads under static condition increases basal cell death rates. However, only the use of a rotating wall vessel induced dose-dependent cell death in response to gentamicin. These data demonstrate directly that there is a dramatic change in the sensitivity of cells to drugs and toxins in 3D cell cultures.

Although preferred embodiments of the present invention have been illustrated in the accompanying drawings and described in the foregoing detailed description, it will be understood that the invention is not limited to the embodiments disclosed, but is capable of numerous rearrangements, modifications and substitutions without departing from the spirit of the invention as set forth and defined by the following claims.

The invention claimed is:

1. A method of studying infectivity of a pathogen in tissues comprising the steps of:
   isolating cells from a host tissue sample;
   placing said isolated host cells into a bioreactor comprising culture medium to form a cell culture;
   applying sedimental shear stress to the cells in the cell culture to form a three-dimensional tissue mass;
   seeding the formed tissue mass in a tissue culture vessel;
   introducing an infectious pathogen into said three-dimensional mass; and
   assaying the infectivity of said infectious pathogen, wherein said assaying comprises the steps of:
      obtaining a measurement of at least one of the following parameters after introducing said infectious pathogen:
         adherence of said infectious pathogen to cultured cells;
         cytokine expression in cultured cells; or
         prostaglandin synthesis in cultured cells; and
      comparing the measurement to a control value of the measured parameter, wherein the control value corresponds to a measurement of the same parameter for a cell culture into which said infectious pathogen has not been introduced.

2. The method of claim 1, optionally comprising a culture matrix that facilitates growth of said host cells.

3. The method of claim 1, wherein the bioreactor is a rotating wall vessel.

4. The method of claim 1, wherein said isolated host cells are epithelial cells.

5. The method of claim 4, wherein said epithelial cells are human intestinal cells.

6. The method of claim 2, wherein said culture matrix consists of microbeads or microcarners.

7. The method of claim 1, wherein said infectious pathogen is selected from the group consisting of viruses, bacteria, protozoa, parasites and fungi.

8. The method of claim 7, wherein said infectious pathogen is *Salmonella typhimurium*.

9. The method of claim 1, wherein said culture medium comprises fetal bovine serum and a tri-sugar based medium comprising fructose, galactose and lactose.

10. The method of claim 6, wherein said microbeads are collagen-coated microbeads.

11. A method of studying the infectivity of a pathogen in tissues comprising the steps of:
   isolating cells from a sample of intestinal epithelial tissue;
   placing said intestinal epithelial cells into a bioreactor comprising culture medium to form a cell culture;
   applying sedimental shear stress to the cells in the cell culture to form a three dimensional tissue mass;
   seeding the formed tissue mass in a tissue culture vessel;
   introducing an infectious pathogen to the formed tissue mass;
   assaying the infectivity of said infectious pathogen, wherein said assaying comprises the steps of:
      obtaining a measurement of at least one of the following parameters after introducing said infectious pathogen:
         adherence of said infectious pathogen to cultured cells;
         cytokine expression in cultured cells; or
         prostaglandin synthesis in cultured cells; and
      comparing the measurement to a control value of the measured parameter, wherein the control value corresponds to a measurement of the same parameter for a cell culture into which said infectious pathogen has not been introduced.

12. The method of claim 11, wherein said infectious pathogen is *Salmonella typhimurium*.

13. A method of measuring the chemosensitivity of tissues to a toxic material comprising:
   isolating cells from a host tissue sample;
   placing said isolated host cells into a bioreactor comprising culture medium to form a cell culture;
   applying sedimental shear stress to the cells in the cell culture to form a three-dimensional tissue mass;
   seeding the formed tissue mass in a tissue culture vessel;
   introducing a toxic material into said three-dimensional tissue mass; and
   assaying the chemosensitivity of said toxic material by obtaining a measurement of cell death among cultured cells after introduction of said toxic material; and
   comparing the measurement to a control value of cell death for a cell culture into which said toxic material has not been introduced.

14. The method of claim 13, optionally comprising a culture matrix that facilitates growth of said host cells.

15. The method of claim 13, wherein said isolated host cells are epithelial cells.

16. The method of claim 15, wherein said epithelial cells are human renal cells.

17. The method of claim 14, wherein said culture matrix consists of microbeads or microcarners.

18. The method of claim 17, wherein said microbeads are collagen-coated microbeads.

19. The method of claim 13, wherein said toxic material is a chemotherapeutic material.

20. The method of claim 19, wherein said chemotherapeutic material is an antibiotic.

21. The method of claim 20, wherein said antibiotic is gentamicin.

22. The method of claim 13, wherein said culture medium comprises fetal bovine serum and DMEM/F12.

23. A method of measuring the chemosensitivity of tissues to a toxic material comprising:
   isolating cells from a sample of human renal epithelial tissue;
   placing said isolated human renal epithelial cells into a bioreactor comprising culture medium to form a cell culture;
   applying sedimental shear stress to the cells in the cell culture to form a three-dimensional tissue mass;
   seeding the formed tissue mass in a tissue culture vessel;
   contacting the three dimensional tissue mass with a toxic material; and assaying the chemosensitivity of said toxic material by obtaining a measurement of cell death among cultured cells after introduction of said toxic material; and comparing the measurement to a control value of cell death for a cell culture into which said toxic material has not been introduced.

24. The method of claim 23, wherein said toxic material is a chemotherapeutic material.

25. The method of claim 24, wherein said chemotherapeutic material is an antibiotic.

* * * * *